(12) United States Patent
Tanabe et al.

(10) Patent No.: US 11,744,455 B2
(45) Date of Patent: Sep. 5, 2023

(54) IMAGE SIGNAL OUTPUT DEVICE AND METHOD, AND IMAGE DATA CONVERSION DEVICE, METHOD, AND PROGRAM

(71) Applicant: NIKON CORPORATION, Tokyo (JP)

(72) Inventors: Yasushi Tanabe, Fujisawa (JP);
Tomoharu Fujiwara, Gyoda (JP);
Mariko Hirokawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 609 days.

(21) Appl. No.: 16/634,481

(22) PCT Filed: Jul. 30, 2018

(86) PCT No.: PCT/JP2018/028512
§ 371 (c)(1),
(2) Date: Jan. 27, 2020

(87) PCT Pub. No.: WO2019/026861
PCT Pub. Date: Feb. 7, 2019

(65) Prior Publication Data
US 2020/0237208 A1 Jul. 30, 2020

(30) Foreign Application Priority Data
Aug. 1, 2017 (JP) .................................. 2017-149212

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0058* (2013.01); *A61B 3/1025* (2013.01);
(Continued)

(58) Field of Classification Search
CPC ... A61B 3/0025; A61B 3/0058; A61B 3/1025; A61B 3/12; A61B 3/14; G06T 7/0012; G06T 2207/30041
(Continued)

(56) References Cited

U.S. PATENT DOCUMENTS

2003/0179211 A1* 9/2003 Wada .................. H04N 9/73
345/589
2006/0192812 A1* 8/2006 Arazaki ............... G06K 15/102
347/41

(Continued)

FOREIGN PATENT DOCUMENTS

JP 2014-217755 A 11/2014

OTHER PUBLICATIONS

Office Action issued in corresponding Japanese Patent Application No. 2019-534512 dated Jun. 29, 2021 with English translation.

*Primary Examiner* — Mohammed A Hasan
(74) *Attorney, Agent, or Firm* — Foley & Lardner LLP

(57) ABSTRACT

An image signal output device including an acquisition section configured to acquire a fundus image, a selection section configured to select a projection for displaying the acquired fundus image from plural projections, a conversion section configured to convert the fundus image into the selected projection, and a processing section configured to output an image signal of the converted fundus image.

6 Claims, 14 Drawing Sheets

(51) Int. Cl.
  *A61B 3/12* (2006.01)
  *A61B 3/14* (2006.01)
  *G06T 7/00* (2017.01)

(52) U.S. Cl.
  CPC .................. *A61B 3/12* (2013.01); *A61B 3/14* (2013.01); *G06T 7/0012* (2013.01); *G06T 2207/30041* (2013.01)

(58) Field of Classification Search
  USPC ....................................................... 351/206
  See application file for complete search history.

(56) References Cited

U.S. PATENT DOCUMENTS

| | | | | |
|---|---|---|---|---|
| 2014/0327877 | A1* | 11/2014 | Hemert | A61B 3/14 351/246 |
| 2015/0091940 | A1* | 4/2015 | Emori | H04N 1/00204 345/629 |
| 2020/0258295 | A1* | 8/2020 | Hirokawa | G06T 17/00 |

* cited by examiner

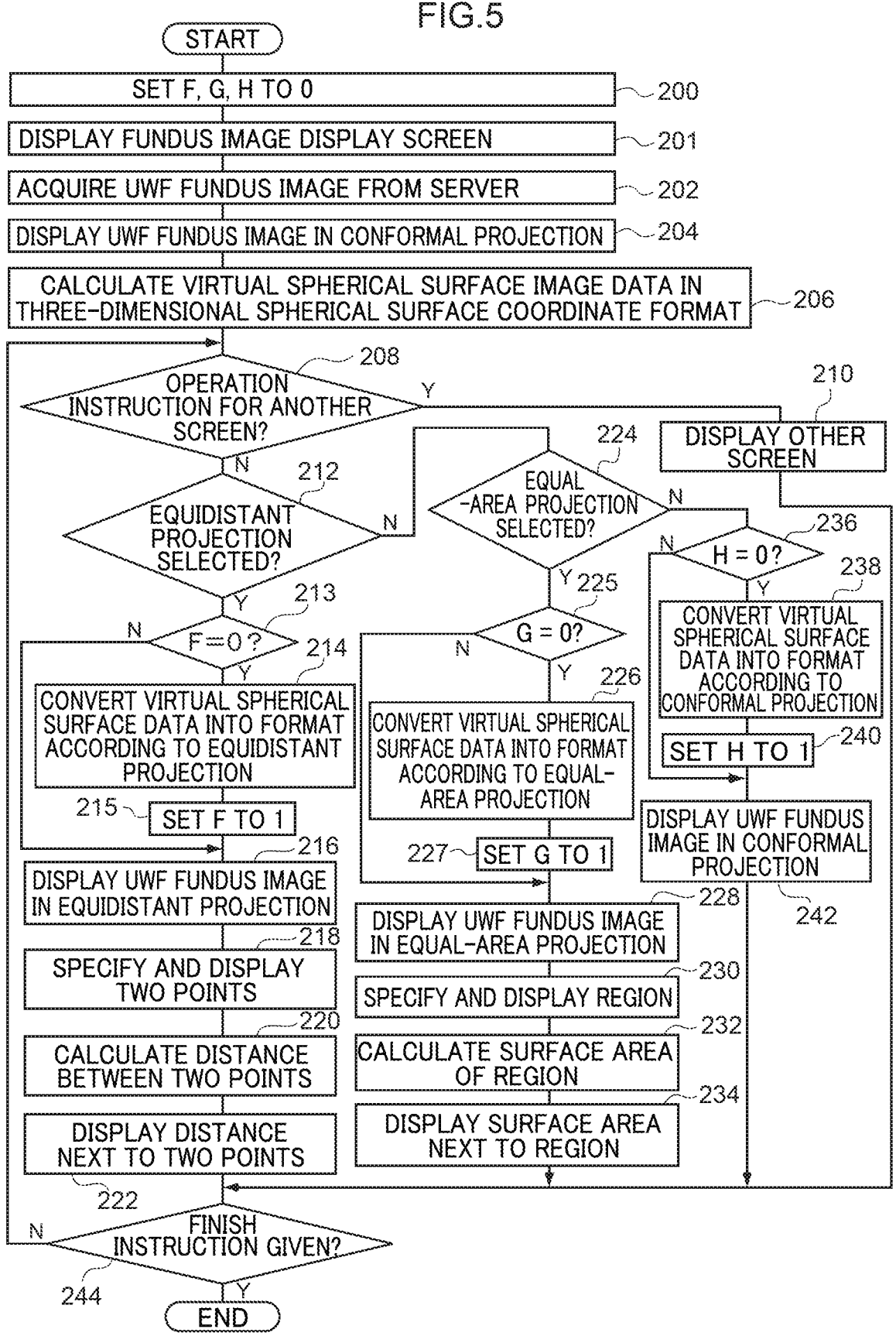

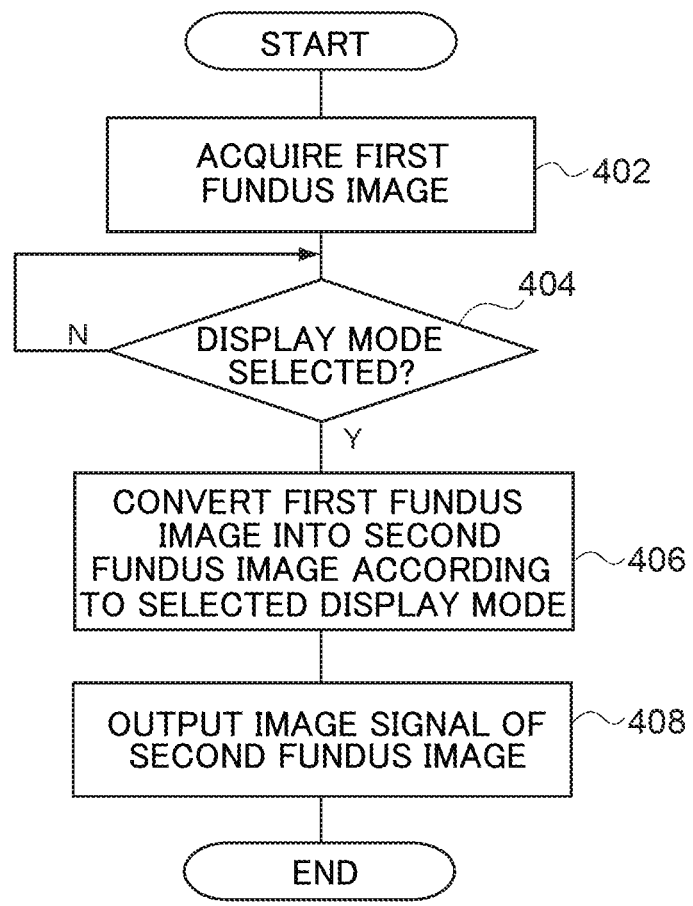

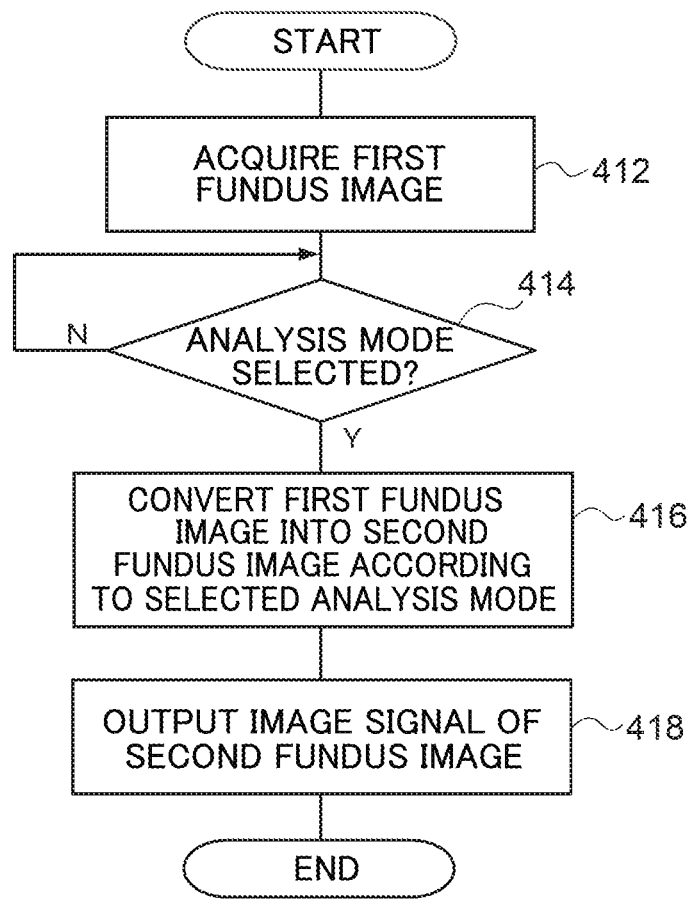

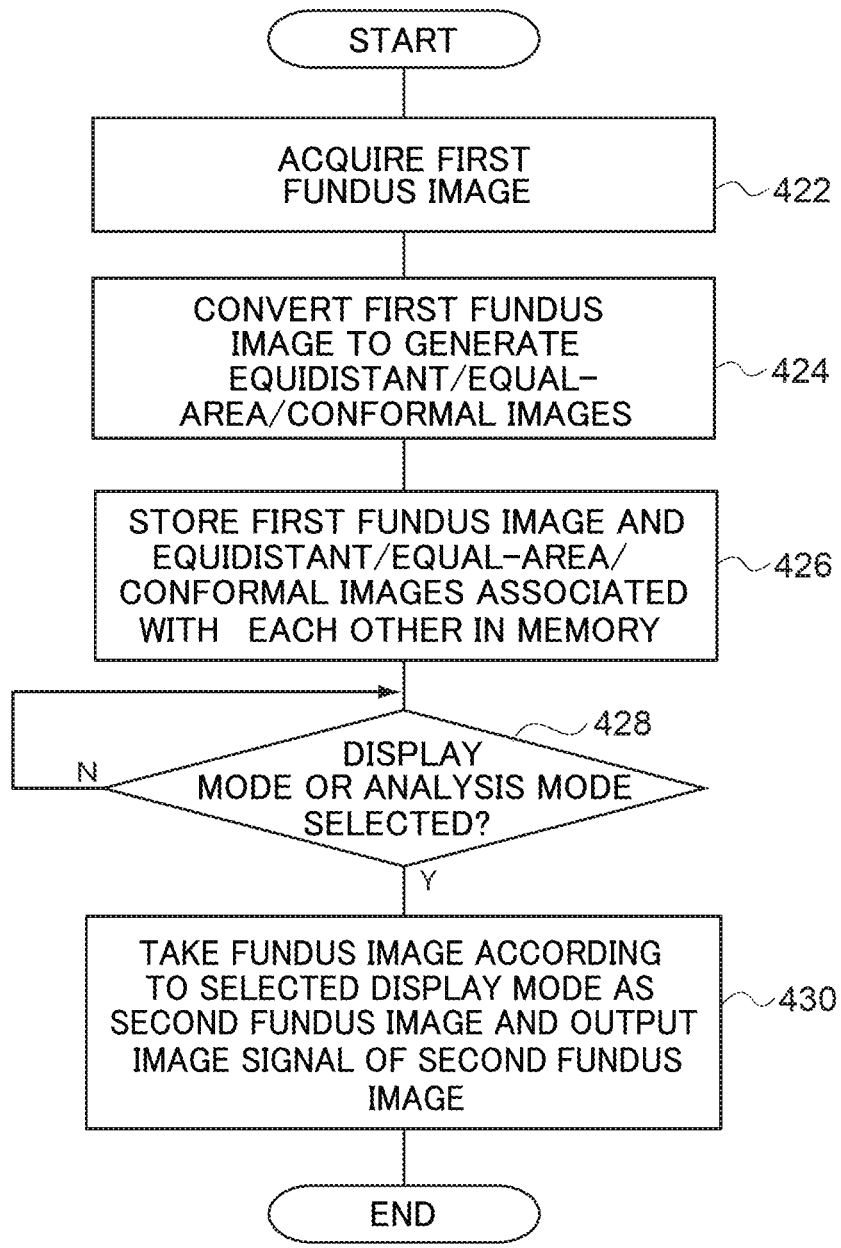

ic imaging device 110.
IMAGE SIGNAL OUTPUT DEVICE AND METHOD, AND IMAGE DATA CONVERSION DEVICE, METHOD, AND PROGRAM

FIELD

The present invention relates to an image signal output device and method, and to an image data conversion device, method, and program.

BACKGROUND ART

In the disclosure of Patent Document 1, the fundus of an eye is imaged and displayed on a display section. When two points on a displayed fundus image are specified, an actual distance in the fundus is calculated from a coordinate distance on a mask display screen on a fundus with a size computed according to a subject eye diopter and an eye axial length, and the coordinate distance between the two specified points on the display screen (see for example Patent Document 1).

PATENT DOCUMENT

Patent Document 1: Japanese Patent Application Laid-Open (JP-A) No. 2006-122160

SUMMARY OF INVENTION

An image signal output device of a first aspect of the technology disclosed herein includes an acquisition section configured to acquire a fundus image, a selection section configured to select a projection for displaying the acquired fundus image from plural projections, a conversion section configured to convert the fundus image into the selected projection, and a processing section configured to output an image signal of the converted fundus image.

An image signal output device of a second aspect includes an acquisition section configured to acquire a conformal fundus image, a selection section configured to select a fundus image projection, a conversion section configured to convert a fundus image into the selected projection, and a processing section configured to output a first image signal of the conformal fundus image acquired by the acquisition section and to output a second image signal of a fundus image converted into the selected projection in cases in which a projection selection is made by the selection section.

An image signal output device of a third aspect includes an acquisition section configured to acquire a fundus image, and a conversion section configured to convert image data of the acquired fundus image into virtual spherical surface image data with three-dimensional spherical surface coordinates, and to convert the converted virtual spherical surface image data into at least one out of two-dimensional coordinate image data according to a conformal projection, two-dimensional coordinate image data according to an equal-area projection, or two-dimensional coordinate image data according to an equidistant projection.

A fourth aspect is a program to cause a computer to function as the acquisition section, the selection section, the conversion section, and the processing section of the image signal output device of the first aspect or the second aspect.

A fifth aspect is a program to cause a computer to function as the acquisition section and the conversion section of the image data conversion device of the third aspect.

An image signal output method of a sixth aspect includes by a computer, acquiring a fundus image, by the computer, selecting a projection to display the acquired fundus image from out of plural projections, by the computer, converting the fundus image into the selected projection, and by the computer, outputting an image signal of the converted fundus image.

An image signal output method of a seventh aspect includes by a computer, acquiring a conformal fundus image, by the computer, selecting a fundus image projection, by the computer, converting a fundus image into the selected projection, and by the computer, outputting a first image signal of the acquired conformal fundus image and outputting a second image signal of the fundus image converted into the projection.

An image data conversion method of an eighth aspect includes: by a computer, acquiring a fundus image, by the computer, converting coordinate data of the acquired fundus image into three-dimensional spherical surface coordinate data with three-dimensional spherical surface coordinates, and converting the converted three-dimensional spherical surface coordinate data into at least one out of coordinate data with two-dimensional coordinates according to a conformal projection, coordinate data with two-dimensional coordinates according to an equal-area projection, or coordinate data with two-dimensional coordinates according to an equidistant projection.

An image signal output device of a ninth aspect includes an acquisition section configured to acquire a fundus image, and a processing section configured to output an image signal of a fundus image of the acquired fundus image converted in an equidistant mode, an equal-area mode, or a conformal mode.

A tenth aspect is a program to cause a computer to function as the acquisition section and the processing section of the image signal output device of the ninth aspect.

An image signal output method of an eleventh aspect includes by a computer, acquiring a fundus image, and by the computer, outputting an image signal of a fundus image of the acquired fundus image converted in an equidistant mode, an equal-area mode, or a conformal mode.

BRIEF DESCRIPTION OF DRAWINGS

FIG. 5 is a flowchart illustrating a fundus image display program executed by a CPU 162 of an image viewer 150.

FIG. 12 is a flowchart illustrating a fundus image display program executed by a CPU 162 of an image viewer 150 according to a sixth modified example.

FIG. 13 is a flowchart illustrating a fundus image display program executed by a CPU 162 of an image viewer 150 according to a seventh modified example.

FIG. 14 is a flowchart illustrating a fundus image display program executed by a CPU 162 of an image viewer 150 according to an eighth modified example.

DESCRIPTION OF EMBODIMENTS

Detailed explanation follows regarding an exemplary embodiment of the present invention, with reference to the drawings.

Figure 1:
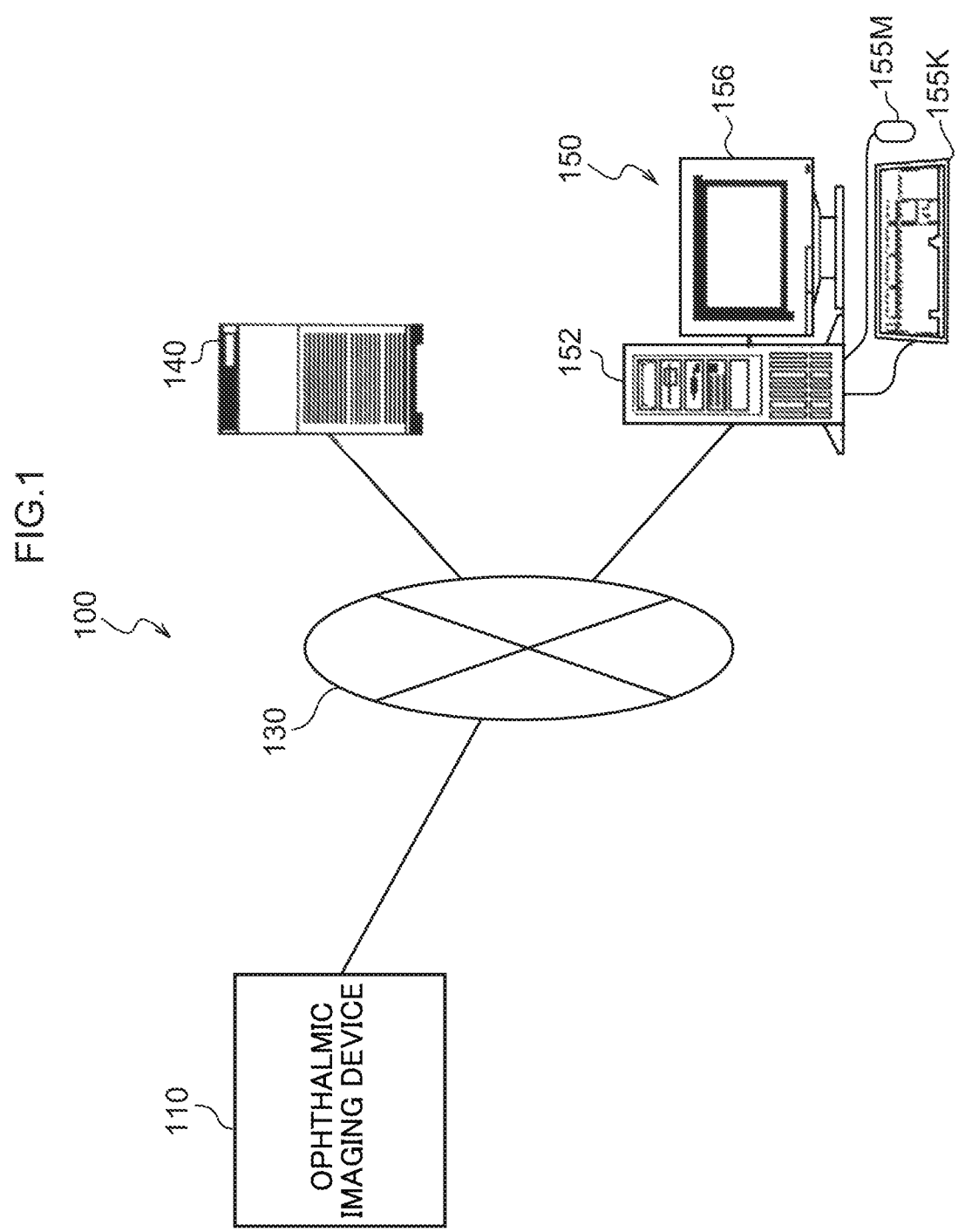
FIG. 1 is a block diagram illustrating a fundus image display system 100.

Explanation follows regarding configuration of a fundus image display system 100, with reference to FIG. 1. As illustrated in FIG. 1, the fundus image display system 100 includes an ophthalmic imaging device 110 that captures a fundus image, an image management server 140 that stores plural fundus images, obtained by imaging the fundi of plural subjects with the ophthalmic imaging device 110, associated with subject IDs, and an image viewer 150 that displays a fundus image acquired by the image management server 140. The ophthalmic imaging device 110, the image management server 140, and the image viewer 150 are mutually connected through a network 130. Note that the image viewer 150 is an example of an image signal output device and an image data conversion device of the technology disclosed herein.

Figure 2:
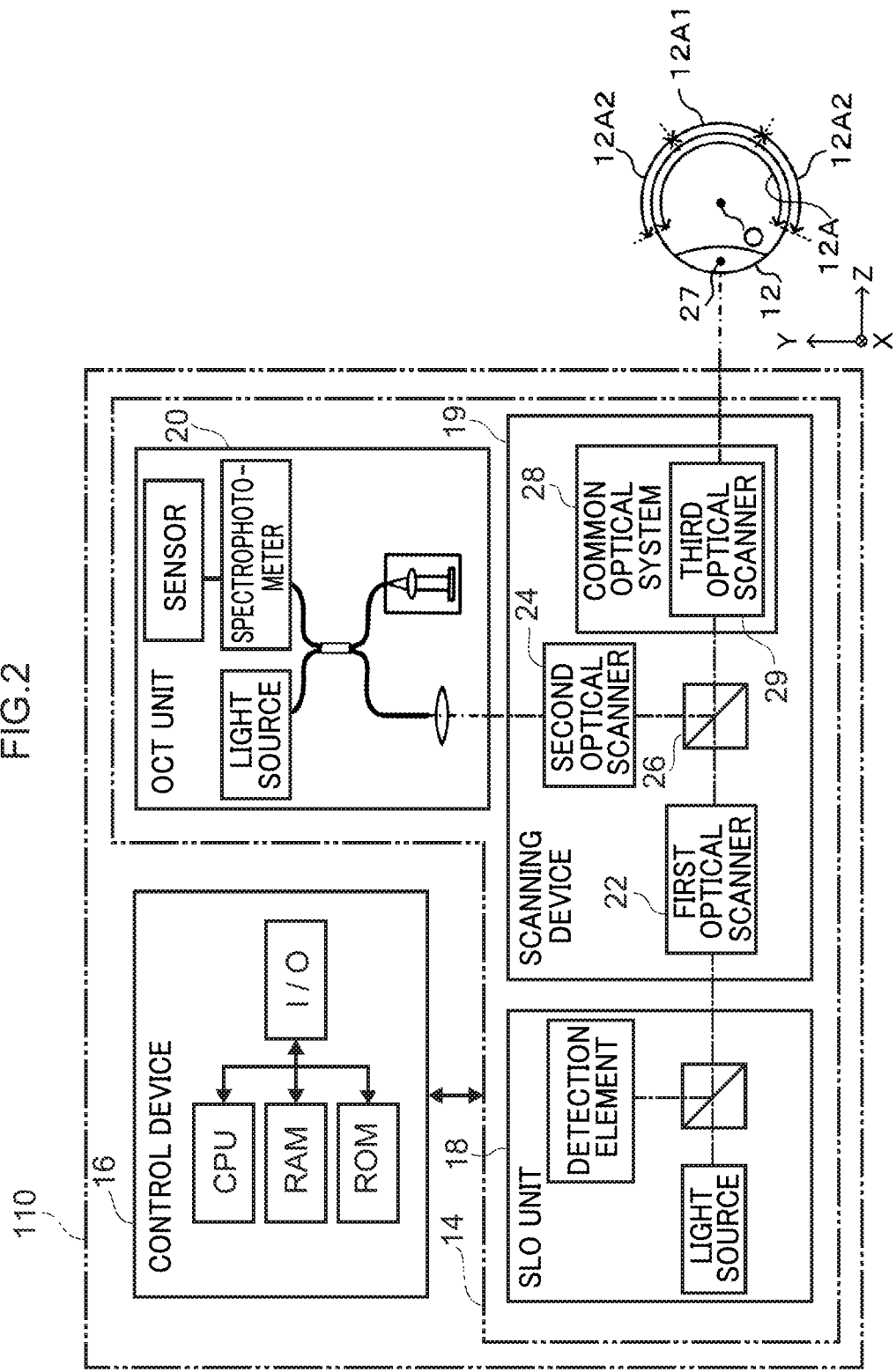
FIG. 2 is a functional block diagram illustrating an example of overall configuration of an ophthalmic imaging device 110.

Explanation follows regarding an example of configuration of the ophthalmic imaging device 110, with reference to FIG. 2. As illustrated in FIG. 2, the ophthalmic imaging device 110 includes a device body 14 that images the fundus of a subject eye, and a control device 16. The control device 16 is configured by a computer including a CPU, RAM, ROM, and an input/output (I/O) port, and is connected to the network 130 through a non-illustrated communication interface (I/F). In the following explanation, "imaging" refers to the acquisition by a user of an image representing an imaging subject using the ophthalmic imaging device 110, and is also referred to as "image capture" on occasion. The device body 14 operates under the control of the control device 16. The device body 14 includes an SLO unit 18, a scanning device 19, and an OCT unit 20.

In the following explanation, when the ophthalmic imaging device 110 is installed on a horizontal plane, the horizontal direction is referred to as the "Y direction", a direction perpendicular to the horizontal direction is referred to as the "X direction", and a direction from the anterior segment through an eyeball center O toward the fundus of a subject eye 12 is referred to as the "Z direction". Accordingly, the X direction is a direction perpendicular to both the Y direction and the Z direction.

The ophthalmic imaging device 110 according to the present exemplary embodiment includes two functions as examples of main functions that can be implemented by the ophthalmic imaging device 110. The first function is a function in which the ophthalmic imaging device 110 operates as a scanning laser ophthalmoscope (hereafter SLO) to perform SLO imaging (this function is referred to hereafter as the SLO imaging system function). The second function is a function in which the ophthalmic imaging device 110 operates as an optical coherence tomography (hereafter OCT) device to perform OCT imaging (this function is referred to hereafter as the OCT imaging system function).

Out of the configuration of the ophthalmic imaging device 110, the SLO imaging system function is implemented by the control device 16, the SLO unit 18, and the scanning device 19 that includes a first optical scanner 22. The SLO unit 18 includes a light source, and a detection element, and the like, and is configured to perform image capture of the fundus of the subject eye 12. Namely, the ophthalmic imaging device 110 operates in the SLO imaging system function to perform image capture in which the fundus (for example an imageable region 12A) of the subject eye 12 serves as an imaging subject. Specifically, light from the SLO unit 18 (referred to hereafter as SLO light) is passed through the pupil of the subject eye 12 by the scanning device 19, is scanned in the X direction (vertical direction) onto the imageable region 12A by the first optical scanner 22, and is scanned in the Y direction (horizontal direction) by a third optical scanner 29. A fundus image configured by the reflected light is acquired by the SLO unit 18. Note that since the SLO imaging system function is a known function, detailed explanation thereof is omitted.

The OCT imaging system function is implemented by the control device 16, the OCT unit 20, and the scanning device 19 that includes a second optical scanner 24. The OCT unit 20 includes a light source, a spectrophotometer, a sensor, a reference optical system, and the like, and is configured to capture images of plural tomographic regions in a fundus layer thickness direction. Namely, the ophthalmic imaging device 110 operates in the OCT imaging system function to capture images of tomographic regions that are regions in the fundus thickness direction (for example the imageable region 12A). Specifically, light from the OCT unit 20 (referred to hereafter as measurement light) is passed through the pupil of the subject eye 12 and onto the imageable region 12A by the scanning device 19 while being scanned in the X direction (vertical direction) by the second optical scanner 24 and being scanned in the Y direction (horizontal direction) by the third optical scanner 29. Light reflected from the measurement light interferes with reference light to generate interference light. The OCT unit 20 detects respective spectral components of the interference light, and the control device 16 employs the detection results thereof to acquire physical quantities (for example a tomographic image) representing the tomographic regions. Note that since the OCT imaging system function is a known function, detailed explanation thereof is omitted.

In the following explanation, the SLO light and the measurement light are both light scanned in two dimensions, namely in the X direction and the Y direction. Accordingly, where it is not necessary to distinguish between the SLO light and the measurement light in the explanation, the SLO light and the measurement light are referred to collectively as scanning light.

Note that in the present exemplary embodiment, the ophthalmic imaging device 110 including functionality that employs scanning light is described as an example. However, there is no limitation to ophthalmic imaging devices including functionality that employs scanning light, and any functionality enabling observation of the subject eye 12 may be adopted. For example, there is no limitation to shining scanning light, and application may be made to any ophthalmic imaging device including functionality that enables observation of the fundus of the subject eye 12 by shining light toward the fundus of the subject eye 12. Namely, there is no limitation to employing light reflected from the subject eye 12 by scanning with scanning light, and functionality to observe the subject eye 12 simply by shining light is also acceptable. There is, moreover, no limitation to shining light into the subject eye 12. For example, functionality to observe the subject eye 12 using light such as fluorescent light generated in the subject eye 12 is also acceptable. Accordingly, light employed when observing the subject eye 12 is a concept encompassing both light reflected from the fundus and light generated at the fundus. This concept is referred to as "light from the subject eye 12" in the following explanation.

Figure 3:
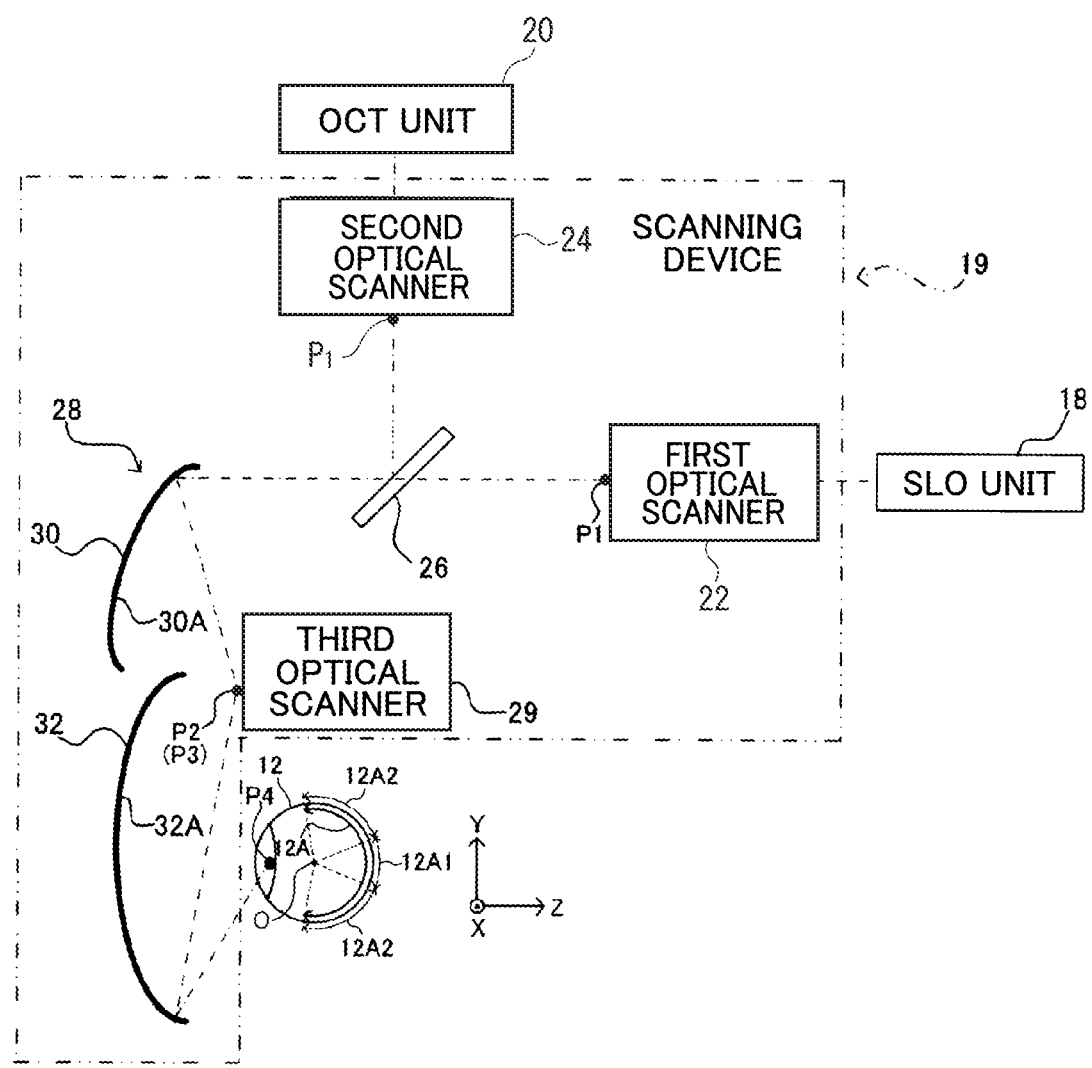
FIG. 3 is a schematic view outlining an example of configuration of a scanning device included in an ophthalmic imaging device 110.

Explanation follows regarding configuration of the scanning device included in the ophthalmic imaging device 110, with reference to FIG. 3. As illustrated in FIG. 3, a common optical system 28 includes a slit mirror 30 and an elliptical mirror 32 as well as the third optical scanner 29. Note that a dichroic mirror 26, the slit mirror 30, and the elliptical mirror 32 are illustrated in an end-on side view. Note that the common optical system 28 may be configured by a set of plural lenses instead of by the slit mirror 30 and the elliptical mirror 32.

The slit mirror 30 includes an elliptical first reflecting face 30A. The first reflecting face 30A has first focal points P1 and a second focal point P2. The elliptical mirror 32 also includes an elliptical second reflecting face 32A. The second reflecting face 32A has a first focal point P3 and a second focal point P4.

The slit mirror 30, the elliptical mirror 32, and the third optical scanner 29 are disposed such that the first focal point P3 and the second focal point P2 are both located at a common position at the third optical scanner 29. The slit mirror 30, the elliptical mirror 32, and the third optical scanner 29 are also disposed such that the second focal point P4 is positioned at the center of the pupil of the subject eye 12. Moreover, the first optical scanner 22, the second optical scanner 24, and the slit mirror 30 are disposed such that the first focal points P1 are positioned at the first optical scanner 22 and the second optical scanner 24.

Namely, the first optical scanner 22, the second optical scanner 24, and the third optical scanner 29 are disposed at conjugate positions to the center of the pupil of the subject eye 12.

Note that the configurations disclosed in Japanese Patent Nos. 3490088 and 5330236 may be employed for the basic configuration of the scanning device 19.

In the present exemplary embodiment, the scanning device illustrated in FIG. 3 has a field of view (FOV) angle of the fundus covering a greater angle than in technology hitherto, thereby enabling observation of a wider range of a fundus region than that achieved by technology hitherto. Explanation follows regarding the wider range of the fundus region, with a distinction being made between an external illumination angle of illumination light shone from the exterior by the ophthalmic imaging device 110 and an internal illumination angle serving as an angle illuminated within the subject eye by this illumination light.

The external illumination angle is an illumination angle of light from the ophthalmic imaging device 110, namely, from the exterior of the subject eye 12. Namely, the external illumination angle is configured by the angle of light shone toward the fundus of the subject eye 12 heading toward a pupil center point 27 (namely, a center point of the pupil as viewed face-on (see also FIG. 2)) of the subject eye 12. The external illumination angle is equivalent to the angle of light reflected from the fundus so as to head from the pupil center point 27, out of the subject eye 12, and toward the ophthalmic imaging device 110.

The internal illumination angle refers to an illumination angle of light effectively imaged when the scanning light is shone onto the fundus of the subject eye 12, with the eyeball center O of the subject eye 12 as a reference position. Although an external illumination angle A and an internal illumination angle B are in a correspondence relationship, since the following explanation relates to the ophthalmic imaging device, the external illumination angle is employed as an illumination angle corresponding to the field of view angle of the fundus.

The ophthalmic imaging device 110 performs image capture in the imageable region 12A (see also FIG. 2), this being a fundus region of the subject eye 12, using the external illumination angle. The imageable region 12A is, for example, the largest region capable of being scanned by the scanning light from the scanning device 19. One example of the imageable region 12A is the external illumination angle A, providing a field of view over a range of approximately 120°. In such cases, the internal illumination angle corresponds to an angle of approximately 160°.

For example, the imageable region 12A can be broadly split into a first imageable region 12A1 and a second imageable region 12A2. The first imageable region 12A1 is a range of a field of view in the vicinity of an axis of vision CL passing through the pupil center point 27 and the center O of the subject eye 12. The second imageable region 12A2 is a peripheral region to the first imageable region 12A1 and is a range in a peripheral field of view away from the axis of vision CL. An example of the external illumination angle corresponding to the first imageable region 12A1 is approximately 300 (corresponding to an internal illumination angle of approximately 45°), and an example of the external illumination angle corresponding to the second imageable region 12A2 is approximately 120° (corresponding to an internal illumination angle of approximately 1600).

A fundus image obtained by performing image capture of the imageable region 12A of the subject eye 12 using the ophthalmic imaging device 110 is a wider region than that of technology hitherto, and is thus referred to hereafter as an ultra-wide field (UWF) fundus image.

Figure 4A:
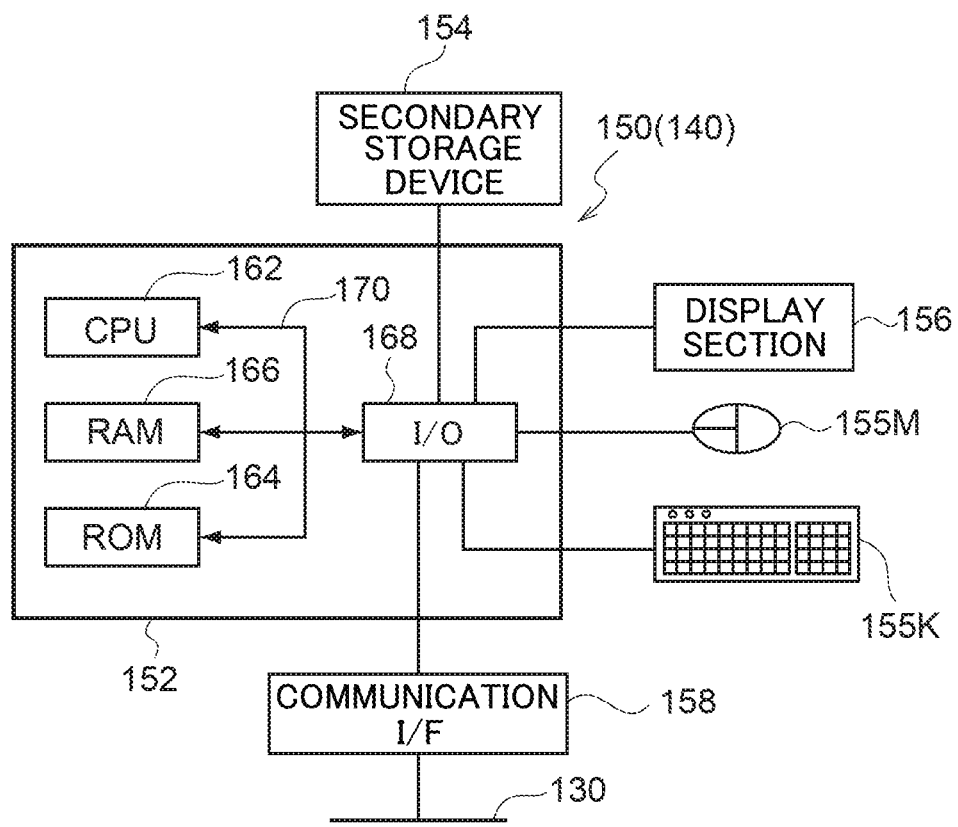
FIG. 4A is a block diagram illustrating configuration of an electrical system of an image viewer 150.

Explanation follows regarding configuration of an electrical system of the image viewer 150, with reference to FIG. 4A. As illustrated in FIG. 4A, the image viewer 150 includes a computer body 152 provided with a CPU 162, RAM 166, ROM 164, and an input/output (I/O) port 168. A secondary storage device 154, a display section 156, a mouse 155M, a keyboard 155K, and a communication interface (I/F) 158 are connected to the input/output (I/O) port 168 of the computer body 152. The input/output (I/O) port 168 of the computer body 152 is connected to the network 130 through the communication interface (I/F) 158, enabling the ophthalmic imaging device 110 and the image management server 140 to communicate with each other. The ROM 164 or the secondary storage device 154 is stored with a fundus image display program, described below. Note that the fundus image display program is an example of a program of the technology disclosed herein.

Figure 4B:
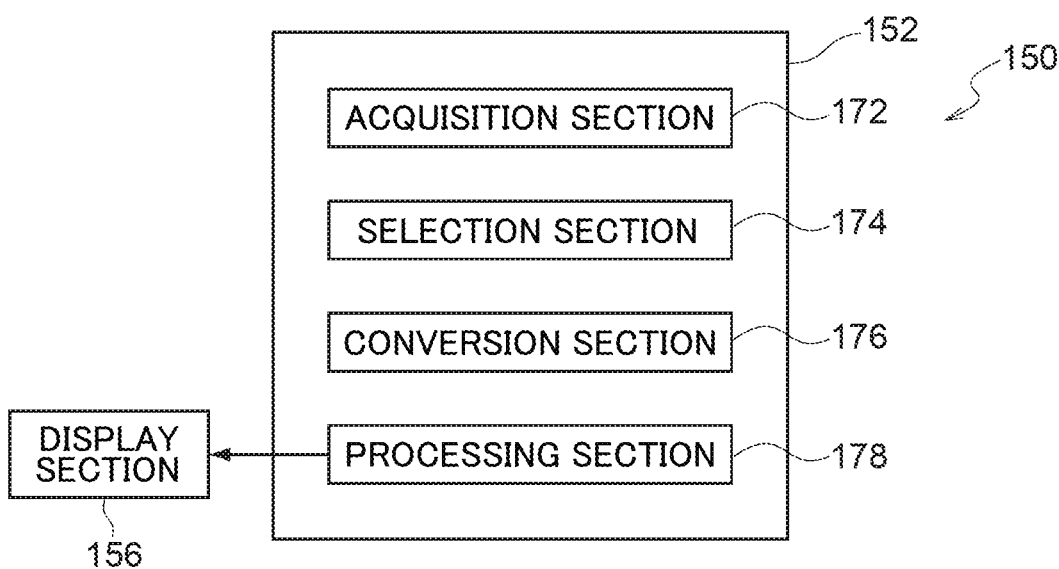
FIG. 4B is a functional block diagram illustrating an image viewer 150.

Explanation follows regarding functional configuration of the fundus image display program executed by the CPU 162 of the image viewer 150, with reference to FIG. 4B. As illustrated in FIG. 4B, the fundus image display program includes an acquisition function, a selection function, a conversion function, and a processing function. The CPU 162 of the image viewer 150 functions as an acquisition section 172, a selection section 174, a conversion section 176, and a processing section 178 by the CPU 162 of the image viewer 150 executing the fundus image display program including these functions. The processing section 178 outputs an image signal to the display section 156 as described later, and the display section 156 displays a fundus image based on the image signal output by the processing section 178.

Note that although the ophthalmic imaging device 110 includes the display section 156 in the present exemplary embodiment, the technology disclosed herein is not limited thereto. Configuration may be made in which the ophthalmic imaging device 110 does not include the display section 156, and a separate display device is provided that is physically independent of the ophthalmic imaging device 110. In such cases, the display device may include an image processing processor unit that operates under the control of the CPU 162, and the image processing processor unit may display a fundus image based on an image signal output by the processing section 178.

Configuration of an electrical system of the image management server 140 is similar to the configuration of the electrical system of the image viewer 150, and so explanation thereof is omitted.

Explanation follows regarding operation of the present exemplary embodiment.

In the present exemplary embodiment, a UWF fundus image is displayed in one projection selected from out of three projections.

Explanation follows regarding fundus image display processing of the fundus image display program executed by the acquisition section 172, the selection section 174, the conversion section 176, and the processing section 178 of the CPU 162 of the image viewer 150, with reference to FIG. 5. When the fundus image display program illustrated in FIG. 5 starts, at step 200 in FIG. 5 the conversion section 176 initializes variables F, G. and H, described later, to zero.

Figure 6:
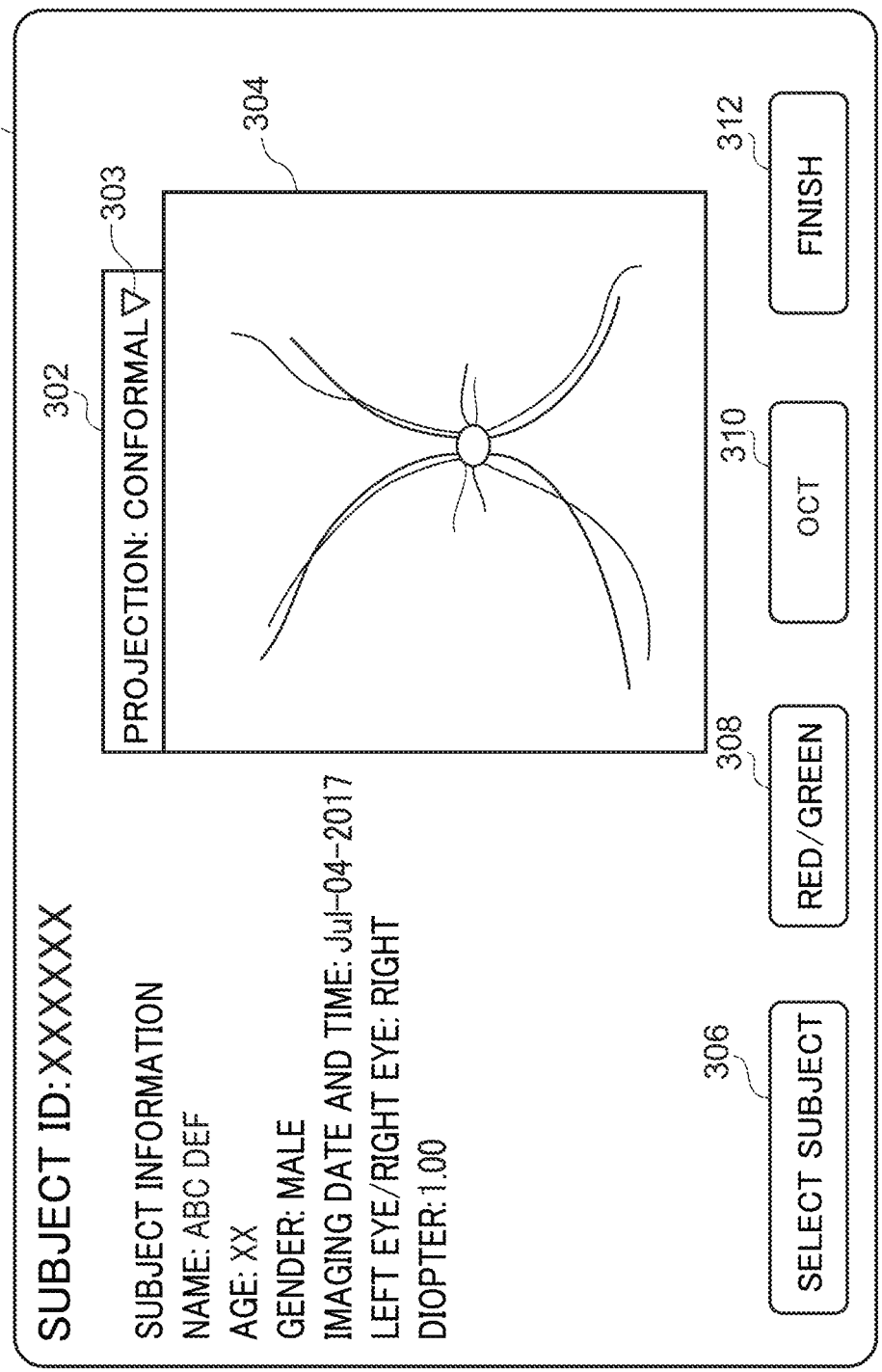
FIG. 6 is a diagram illustrating a fundus image display screen 300 in a conformal display mode.

At step 201, the processing section 178 displays a fundus image display screen 300 illustrated in FIG. 6 on a screen of the display section 156.

As illustrated in FIG. 6, the fundus image display screen 300 includes a region displaying a subject ID, subject information (name, age, gender, imaging date and time, left eye/right eye distinguishers, diopters, and so on), a fundus image display region 304 to display a UWF fundus image, a projection selection region 302 to select one projection from out of the three projections mentioned above, a subject selection button 306 to select a subject, a red/green balance specify button 308 to specify the red and green balance in the UWF fundus image, an OCT image display instruction button 310 to display an OCT image, and an end instruction button 312 to end the fundus image display processing. Buttons relating to autofluorescence (AF) images, fluorescein angiography (FA), indocyanine green chorioangiography (ICG) and the like may also be provided.

Various icons (including buttons to zoom in, zoom out, shift screens, add a description, attach to an email, add freehand annotations, and switch between left and right, and icons to perform electronic medical record functionality such as referring to past records) may be displayed at an edge of the screen.

Note that the fundus image display screen 300 includes three display modes (display configurations) employing the three projections, these being: an equal-area display mode in which a UWF fundus image is displayed according to an equal-area projection; an equidistant display mode in which the UWF fundus image is displayed according to an equidistant projection; and a conformal display mode in which the UWF fundus image is displayed according to a conformal projection. The fundus image display screen 300 performs display on the processing section 178 based on the image signal output by the display section 56.

In the equal-area display mode, the fundus image display screen 300 displays the UWF fundus image according to an equal-area projection (Lambert azimuthal equal-area projection) such that a ratio of a surface area on the fundus to a corresponding surface area in the image is the same everywhere, regardless of the size of the surface area. This is a display mode for correctly ascertaining the surface area of the fundus or a selected specific region of the fundus.

In the equidistant display mode, the fundus image display screen 300 displays the UWF fundus image according to an equidistant projection (azimuthal equidistant projection) such that a ratio of the distance from a point corresponding to the eye axial center of the fundus to another point in the image against the distance from the eye axial center to another point of the fundus is the same everywhere, regardless of the distance. This is a display mode for correctly ascertaining the distance between any given two points on the fundus.

In the conformal display mode, the fundus image display screen 300 displays the UWF fundus image according to a conformal projection (stereographic projection) such that angles in the image correspond to angles in the fundus. This is a display mode for correctly ascertaining directions in the fundus (for example the directions of blood vessels, the orientation of the optical nerve, and the like).

At step 202, when a subject ID is input and an instruction to display a fundus image corresponding to the subject ID is input, the acquisition section 172 acquires a UWF fundus image corresponding to the subject ID from the image management server 140 via the communication interface (I/F) 158. As described above, the UWF fundus image is image data based on a two-dimensional coordinate format.

At step 204, the UWF fundus image is displayed on the display section 156. Specifically, the processing section 178 outputs an image signal for the UWF fundus image to the display section 156. The display section 156 displays the UWF fundus image on the fundus image display region 304 based on the output image signal. The fundus image displayed at step 204 is a UWF fundus image obtained by the ophthalmic imaging device 110. The UWF fundus image is configured by coordinate data using a two-dimensional coordinate format. This is since the ophthalmic imaging device 110 scans the fundus in a perpendicular direction (the Y direction) and in a horizontal function perpendicular to the perpendicular direction (the X direction).

The UWF image is an image obtained using the SLO imaging system function of the ophthalmic imaging device 110. The SLO imaging system function scans the fundus with a laser beam pivoting about the pupil of the eyeball. Accordingly, the fundus surface of the eyeball is projected onto a flat plane as a stereo UWF fundus image. Angles in the UWF fundus image are therefore the same as those on the eyeball surface, but the surface areas and distances differ from those in the eyeball. Namely, the UWF fundus image obtained using the SLO imaging system function is a fundus image in a conformal projection in which angles are displayed correctly.

At step 206, the conversion section 176 calculates (converts) the image data of the UWF fundus image acquired at step 202 into virtual spherical surface image data in a three-dimensional spherical surface coordinate format. A virtual spherical surface is data expressing a three-dimensional shape of an eyeball model. An eyeball model that is a standard eyeball model customized using unique subject data, such as the age, ethnicity, and eye axial length of the subject, may configure the virtual spherical surface.

Specifically, first coordinate data X0, Y0 (unit: pixels) of the two-dimensional coordinates of the UWF fundus image are converted into X, Y (unit: rad).

In the two-dimensional coordinates of the UWF fundus image, the vertical pixel counts are called rows, and the widthwise pixel counts are called cols.

When the ophthalmic imaging device 110 scans the fundus, the maximum amplitude (angle) in the perpendicular direction (X direction) from the eye axis is θ rows, and the maximum amplitude (angle) in the horizontal direction (Y direction) from the eye axis is θ cols.

X, Y are expressed as follows.

$$X=((X0-(\text{rows}/2))/(\text{rows}))*(1/\theta \text{ rows})$$

$$Y=((Y0-(\text{cols}/2))/(\text{cols}))*(1/\theta \text{ cols})$$

θ cols=100/180 (rad) (in the case of an external illumination angle equivalent to 100°).

Then, virtual spherical surface image data x, y, z is obtained as follows for the three-dimensional spherical surface coordinates.

$$x=2X/(1+X2+Y2)$$

$$y=2Y/(1+X2+Y2)$$

$$z=(-1+X2+Y2)/(1+X2+Y2)$$

Note that U.S. Pat. Nos. 8,422,750 and 9,649,031 may be employed as a method for converting the UWF fundus image data into the virtual spherical surface image data with three-dimensional spherical surface coordinates. The disclosures of U.S. Pat. No. 8,422,750, filed on Apr. 16, 2013, and U.S. Pat. No. 9,649,031, filed on May 16, 2017 are incorporated in their entireties by reference herein.

At step 208, the selection section 174 determines whether or not an operation instruction for another screen has been given. Specifically, the selection section 174 determines whether or not an operation instruction for another screen has been given by determining whether or not any of the subject selection button 306, the red/green balance specify button 308, the OCT image display instruction button 310, or the like has been clicked.

In cases in which an operation instruction for another screen is determined to have been given at step 208, at step 210 the processing section 178 outputs data for the other screen to the display section 156, and this other screen is displayed on the display section 156.

For example, in cases in which the subject selection button 306 has been clicked, IDs and subject information for each of plural subjects are displayed overlaid on the fundus image display screen 300.

In cases in which the red/green balance specify button 308 has been clicked, a non-illustrated slider to change the red and green balance of the UWF fundus image displayed on the fundus image display region 304 is displayed overlaid on the fundus image display screen 300, and the red and green balance of the UWF fundus image is changed according to the operation position of the slider.

In cases in which the OCT image display instruction button 310 has been clicked, the ophthalmic imaging device 110 executes the OCT imaging function to acquire a tomographic image corresponding to a specified portion in the UWF fundus image, and a display screen to display the acquired tomographic image is displayed.

After step 210, the fundus image display processing proceeds to step 244.

In cases in which an operation instruction for another screen is determined not to have been given at step 208, the selection section 174 determines whether or not equidistant projection has been selected.

Figure 7:
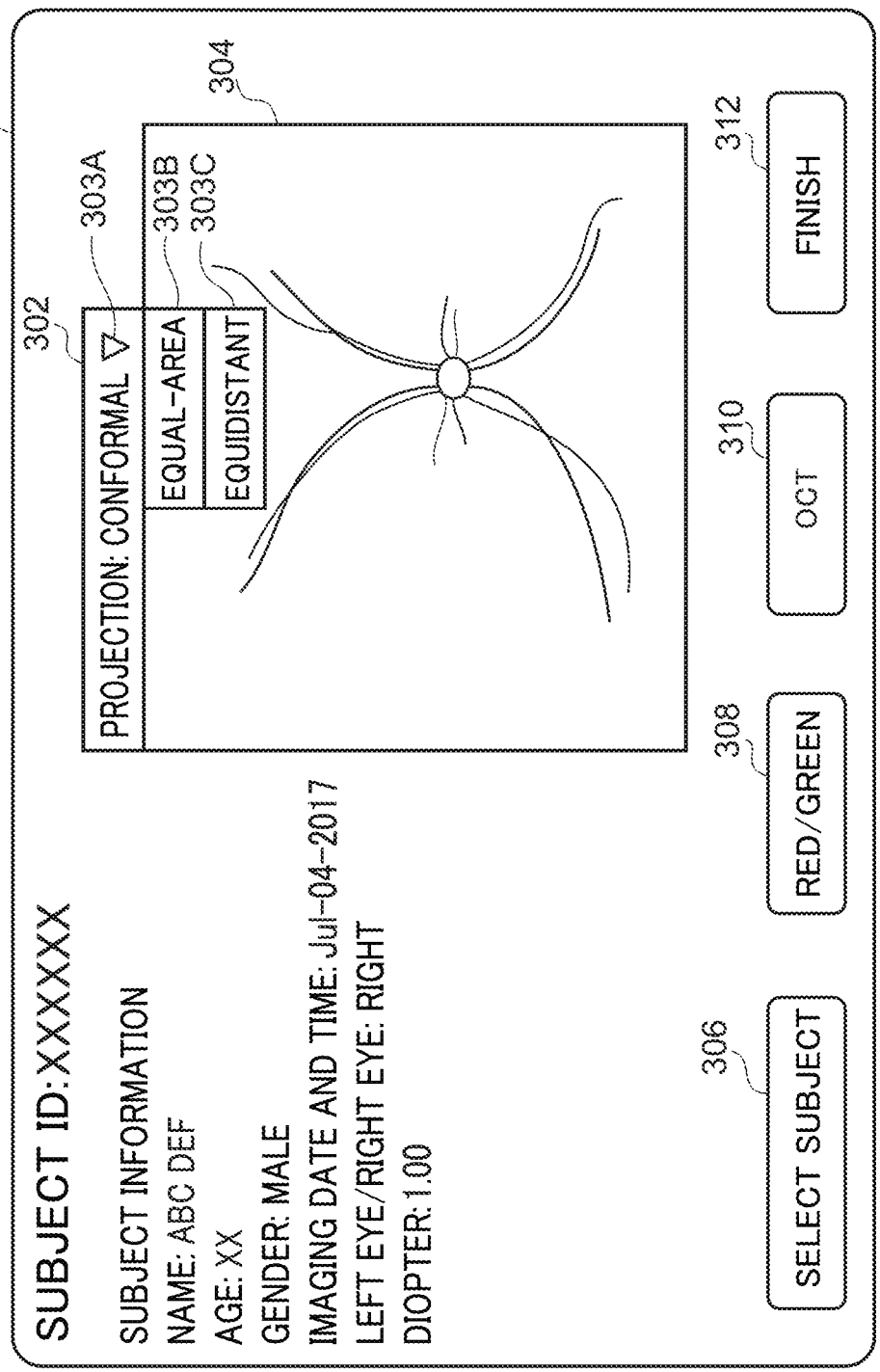
FIG. 7 is a diagram illustrating a fundus image display screen 300 when a projection selection region 302 has been clicked to display selection buttons to select respective projections.

As illustrated in FIG. 6, an item display instruction button 303 to instruct respective items representing the three projections is displayed in the projection selection region 302. When the item display instruction button 303 is clicked, a pulldown menu for the three projections is displayed as illustrated in FIG. 7.

The pulldown menu includes a conformal projection instruction button 303A to instruct conformal projection, an equal-area projection instruction button 303B to instruct equal-area projection, and an equidistant projection instruction button 303C to instruct equidistant projection.

At step 212, the selection section 174 determines whether or not the equidistant projection instruction button 303C has been clicked in order to determine whether or not the equidistant display mode has been selected.

In cases in which determination is made that the equidistant display mode has not been selected at step 212, at step 224 the selection section 174 determines whether or not the equal-area projection instruction button 303B has been clicked in order to determine whether or not the equal-area display mode has been selected.

In cases in which determination is not made that the equal-area display mode has been selected at step 224, since the conformal projection instruction button 303A has been clicked to select the conformal display mode, the fundus image display processing proceeds to step 236.

In cases in which the equidistant projection is determined to have been selected at step 212, at step 213 the conversion section 176 determines whether or not the variable F is 0. In cases in which the variable F is 0, at step 214 the conversion section 176 converts virtual spherical surface image data, this being three-dimensional spherical surface coordinate data, into an equidistant image data format according to the equidistant projection in the following manner.

Specifically, first, the virtual spherical surface image data x, y, z are converted into polar coordinates as follows.

$$\psi = \sin^{-1}(z/\sqrt{(x2+y2+z2)})$$

$$\lambda = \cos^{-1}(x/\sqrt{(x2+y2)})(y \geq 0)$$

$$= -\cos^{-1}(x/\sqrt{(x2+y2+z2)})(y<0)$$

Herein, $c = \cos^{-1}(\sin \psi_0 \sin \psi + \cos \gamma_0 \cos \psi \cos(\lambda - \lambda_0))$ If k'=c/sin (c), equidistant image data X, Y according to the equidistant projection is as follows.

$$X = -k'\{\cos \psi_0 \sin \psi - \sin \psi_0 \cos \psi \cos(\lambda - \lambda_0)\}$$

$$Y = -k' \{\cos \psi_0 \sin \psi(\lambda - \lambda_0)\}$$

$\psi_0 = -\pi/2, \lambda_0 = \pi$ are entered to obtain the equidistant image data X, Y.

At step 215, the conversion section 176 sets the variable F to 1. This stops the conversion processing of step 214 from being repeatedly executed when affirmative determination is repeated at step 212. In cases in which F is not determined to be 0 at step 213, the fundus image display processing skips steps 214 and 215 and proceeds to step 216.

Figure 8:
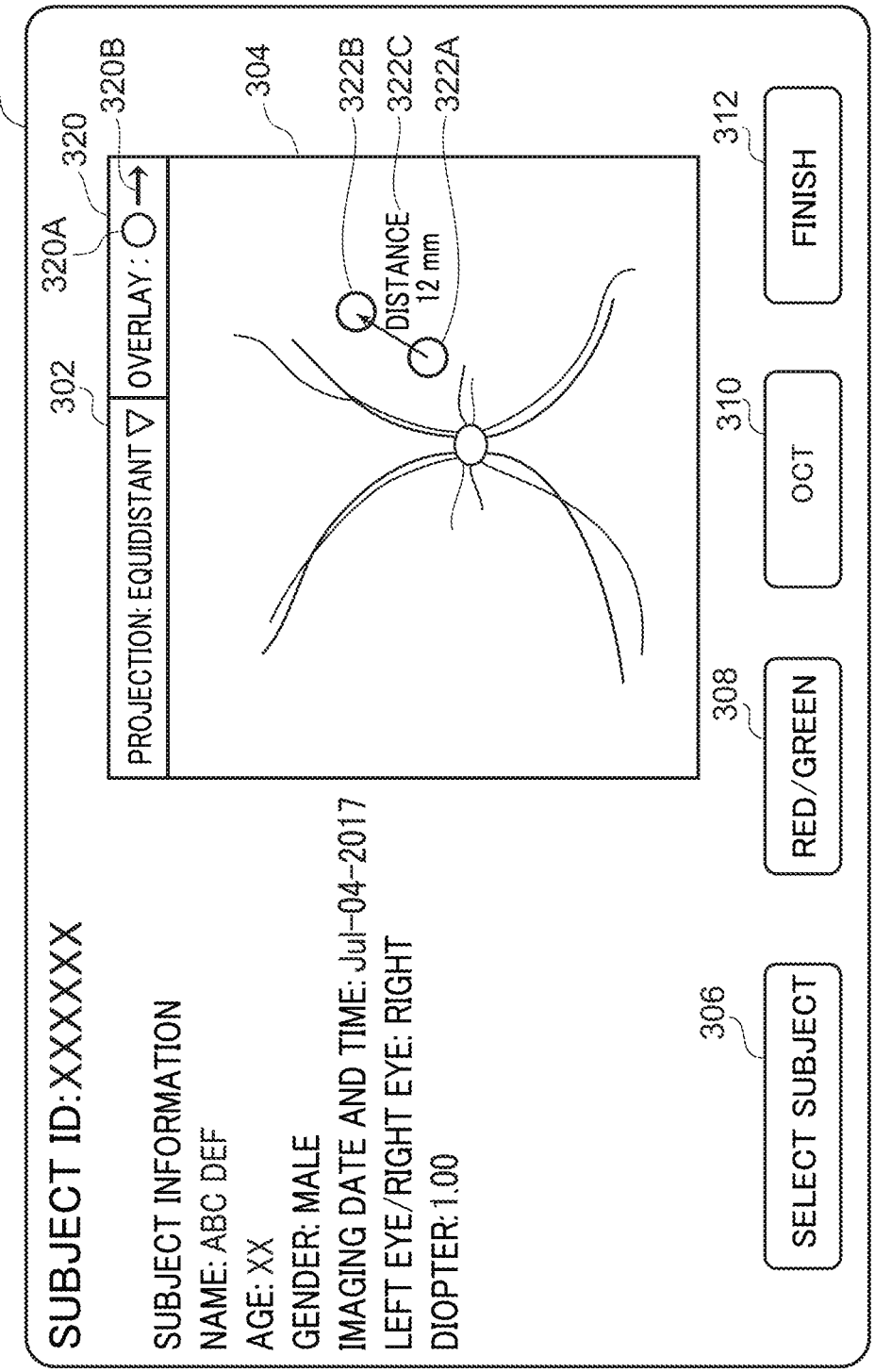
FIG. 8 is a diagram illustrating a fundus image display screen 300 in an equidistant display mode in which a UWF fundus image is displayed in an equidistant projection.

At step 216, as illustrated in FIG. 8, the processing section 178 outputs a signal to the display section 156 including an image signal of the equidistant image data X, Y converted at step 214 to the display section 156 to generate the fundus image display screen 300 in the equidistant display mode in which the converted UWF equidistant fundus image is displayed in the fundus image display region 304. The display section 156 displays the fundus image display screen 300 in the equidistant display mode in which the converted UWF equidistant fundus image is displayed in the fundus image display region 304.

At step 218, the processing section 178 outputs a signal to the display section 156 to specify and display two points. The display section 156 specifies and displays the two points based on the input signal.

As illustrated in FIG. 8, when the fundus image display screen 300 is in the equidistant display mode, a distance calculation icon region 320 is provided next to the projection selection region 302 to execute a user interface to specify two points and instruct calculation of the distance between the two points. A point specify button 320A to specify points and a distance calculation button 320B to instruct calculation of the distance between two points are displayed in the distance calculation icon region 320. The user drags the point specify button 320A so as to drag to a desired point in the fundus image display region 304. This is repeated for a total of two times in order to specify two points 322A, 322B.

When the user drags and drops the distance calculation button 320B between the two points on the fundus image display region 304, at step 220 the processing section 178 calculates the distance between the two points specified at step 218 based on the equidistant image data X, Y converted at step 214.

At step 222, the processing section 178 displays a value for the distance calculated at step 220 (for example, 12 mm) next to the two points 322A, 322B on the fundus image display region 304. The fundus image display processing then proceeds to step 244.

Steps 218 to 222 may be repeated plural times to specify plural sets of two points, calculate the distance between the two points in each set, and display values calculated as the distances next to each set of two points.

There is no limitation to two points being specified. In cases in which a lesion site in the fundus of the subject has been diagnosed and the lesion site has been stored in advance, at step 218 the image viewer ISO may display two points at the pre-stored site. The user adjusts the two points being displayed while viewing the lesion site in the actual fundus image. In cases in which no adjustment is needed, the distance between the two points is calculated as-is.

In cases in which the equal-area projection is determined to have been selected at step 224, at step 225 the conversion section 176 determines whether or not the variable G is 0. In cases in which the variable G is 0, at step 226 the conversion section 176 converts the virtual spherical surface image data into an equal-area image data format according to the equal-area projection in the following manner.

Specifically, the conversion section 176 converts the virtual spherical surface image data x, y, z into equal-area image data according to the equal-area projection by performing the following conversion.

$X = (\sqrt{(2/(1-z))}) * x$ $Y = (\sqrt{(2/(1-z))}) * y$

At step 227, the conversion section 176 sets the variable G to 1. The fundus image display processing then proceeds to step 228.

In cases in which the variable G is not determined to be 0 at step 225, the fundus image display processing skips step 226 and step 227 and proceeds to step 228.

At step 228, the processing section 178 generates a fundus image display screen 300 in the equal-area display mode in which a UWF equal-area fundus image converted into the equal-area projection is displayed in the fundus image display region 304, based on the equal-area image data X, Y converted at step 226, and also outputs data for the fundus image display screen 300 including an image signal for the converted equal-area image data to the display section 156. The display section 156 displays the fundus image display screen 300. The UWF fundus image is thus displayed in the equal-area projection.

At step 230, the processing section 178 outputs a signal for region specification and display to the display section 156. The display section 156 specifies and displays a region based on the input signal.

Figure 9:
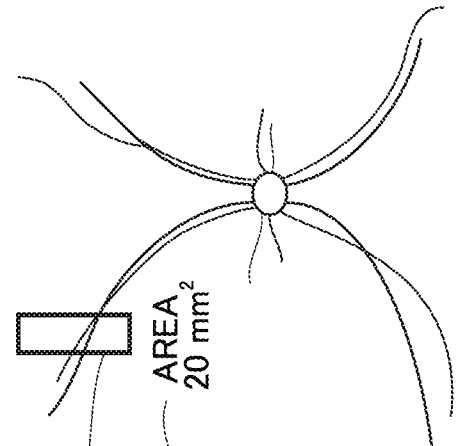
FIG. 9 is a diagram illustrating a fundus image display screen 300 in an equal-area display mode in which a UWF fundus image is displayed in an equal-area projection.

As illustrated in FIG. 9, when the fundus image display screen 300 is in the equal-area display mode, a surface area calculation icon region 330 is displayed next to the projection selection region 302 to execute a user interface to specify an area and calculate the surface area of this area. An area specify button 330A to specify an area is displayed in the surface area calculation icon region 330. The user drags and drops the area specify button 330A at a desired region in the fundus image display region 304. The user then adjusts the size of the area specify button 330A after dropping.

At step 232, the processing section 178 calculates the surface area of a region 330B specified at step 230 based on the equal-area image data X, Y converted at step 226, and at step 234, the processing section 178 displays the value (for example 200 mm) of the surface area at 330C next to the region 330B on the screen of the display section 156. The fundus image display processing then proceeds to step 244.

Steps 230 to 234 may be repeated plural times to specify a set of plural areas, calculate the surface area of each area, and display values calculated as the surface area next to each of the areas.

There is no limitation to an area being specified. In cases in which a lesion site in the fundus of the subject has been diagnosed and the lesion site has been stored in advance, at step 218 the image viewer 150 may display a region of the pre-stored site. The user adjusts the displayed region while viewing the lesion site in the actual fundus image. In cases in which no adjustment is needed, the surface area of the area is calculated as-is.

In cases in which the equidistant projection is determined not to have been selected at step 212 and the equal-area projection is determined not to have been selected at step 224, determination may be made that the conformal projection instruction button 303A has been clicked to select the conformal projection. The fundus image display processing proceeds to step 236.

At step 236, the conversion section 176 determines whether or not the variable H is 0. In cases in which the variable H is 0, at step 238 the conversion section 176 converts the virtual spherical surface image data, this being three-dimensional spherical surface coordinate data, into a conformal image data format according to the conformal projection in the following manner. Note that the UWF fundus image acquired at step 202 may be employed as-is without converting the virtual spherical surface image data into the conformal image data format.

The virtual spherical surface image data is converted into the conformal image data format in the following manner.

Specifically, the conversion section 176 converts the virtual spherical surface image data x, y, z into conformal image data according to the conformal projection by performing the following conversion.

$$X=x/(1-z)$$

$$Y=y(1-z)$$

At step 240, the conversion section 176 sets the variable H to 1. The fundus image display processing then proceeds to step 242.

In cases in which the variable H is determined not to be 0 at step 236, the fundus image display processing skips steps 238 and 240 and proceeds to step 242.

At step 242, the processing section 178 generates a fundus image display screen 300 in the conformal display mode, in which a UWF conformal fundus image converted from the UWF fundus image into the conformal projection is displayed in the fundus image display region 304, based on the conformal image data X, Y converted at step 238, and outputs data for the fundus image display screen 300 including an image signal for the converted conformal image data to the display section 156. The display section 156 displays the fundus image display screen 300. The UWF fundus image is thus displayed in the conformal projection. The fundus image display processing then proceeds to step 244.

Although not illustrated in the drawings, the conformal image data may be employed to calculate the direction between two specified points (the orientation of a straight line defined by two specified points), or to calculate an angle defined by three specified points (for example, when three points, these being a point A, a point B, and a point C, have been specified, the angle ∠ABC).

At step 244, the selection section 174 determines whether or not the end instruction button 312 has been clicked in order to determine whether or not a finish instruction has been given. In cases in which determination is made that a finish instruction has not been given at step 244, processing returns to step 208 and the processing described above (step 208 to step 244) is executed. In cases in which determination is made that a finish instruction has been given at step 244, the processing is ended.

The equidistant image data converted according to equidistant projection has been described as being employed in display of the fundus image in the equidistant mode and also when calculating the distance between two points on the fundus. However, there is no limitation thereto, and the equidistant image data converted according to equidistant projection may be employed when calculating the distance between two points on the fundus, while a fundus image converted so as to give the user the impression of an equidistant mode screen may be employed for the fundus image in the equidistant mode instead of an image converted according to equidistant projection (a fundus image converted not into a true equidistant projection, but by a conversion method close to that of an equidistant projection).

Similarly, the equal-area image data converted according to equal-area projection has been described as being employed in display of the fundus image in the equal-area mode and also when calculating the surface area of a region of the fundus. However, there is no limitation thereto, and the equal-area image data converted according to equal-area projection may be employed when calculating the surface area of the fundus, while a fundus image converted so as to give the user the impression of an equal-area mode screen may be employed for the fundus image in the equal-area mode instead of an image converted according to equal-area projection (a fundus image converted not into a true equal-area projection, but by a conversion method close to that of an equal-area projection).

Similarly, the conformal image data converted according to conformal projection has been described as being employed in display of the fundus image in the conformal mode and also when calculating the direction between two points or an angle defined by three points on the fundus. However, there is no limitation thereto, and the conformal image data converted according to conformal projection may be employed when calculating an angle on the fundus, while a fundus image converted so as to give the user the impression of a conformal mode screen may be employed for the fundus image in the conformal mode instead of an image converted according to the conformal projection (a fundus image converted not into a true conformal projection, but by a conversion method close to that of a conformal projection).

In the present exemplary embodiment as described above, the UWF fundus image is displayed as a fundus image converted according to equal-area projection such that the ratio of a surface area on the fundus and a corresponding surface area in the image is the same everywhere, regardless of the size of the surface area. This thereby enables accurate surface area measurement and presentation.

Moreover, the UWF fundus image is displayed as a fundus image convened according to equidistant projection such that the distance between two points on the fundus appears correctly. This thereby enables accurate distance measurement and presentation.

Moreover, in the present exemplary embodiment, the UWF fundus image is displayed as a UWF fundus image converted according to a projection selected from out of equal-area projection, equidistant projection, or conformal projection. This enables the UWF fundus image to be displayed such that whichever out of surface area, direction, or distance the user desires appears correctly.

Moreover, in the present exemplary embodiment, two-dimensional coordinate image data of the UWF fundus image obtained by the ophthalmic imaging device 110 is converted into virtual spherical surface image data with three-dimensional spherical surface coordinates, and the converted virtual spherical surface image data is converted into image data according to the equal-area projection, image data according to the equidistant projection, and image data according to the conformal projection. Accordingly, the image data converted from the virtual spherical surface image data enables the UWF fundus image to be displayed as an image according to equal-area projection, equidistant projection, and conformal projection.

MODIFIED EXAMPLES

Explanation follows regarding modified examples.

First Modified Example

Figure 10:
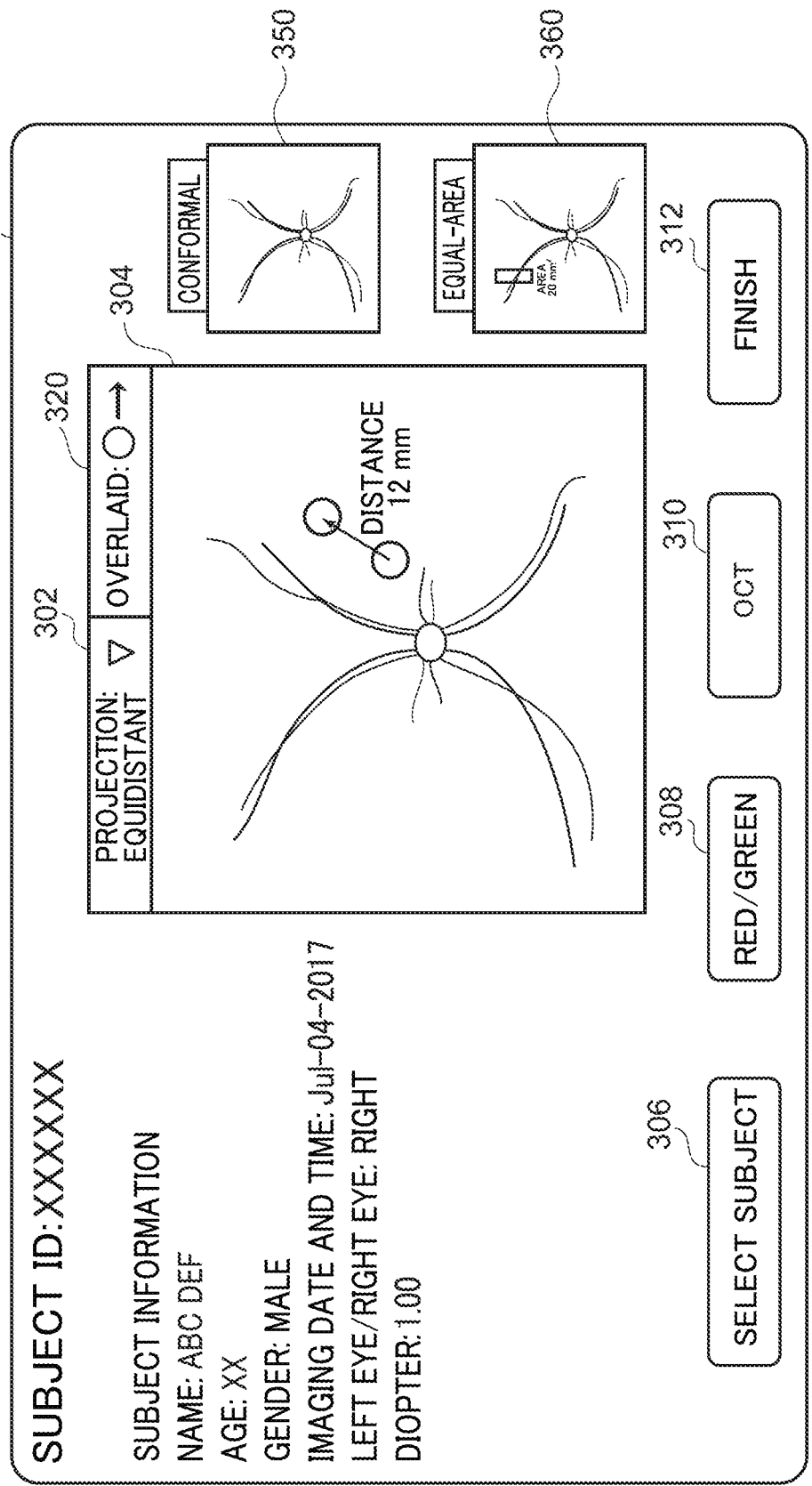
FIG. 10 is a diagram illustrating a fundus image display screen 300 in an equidistant display mode according to a first modified example.

Explanation follows regarding a fundus image display screen 300 according to a first modified example, with reference to FIG. 10. In the exemplary embodiment described above, only a UWF fundus image according to a projection selected from the three projections is displayed on the fundus image display screen 300. The technology disclosed herein is not limited thereto, and UWF fundus images may be displayed in projections that have not been selected as well as a projection that has been selected. Specifically, in the modified example illustrated in FIG. 10, the fundus image display screen 300 includes the fundus image display region 304 of the exemplary embodiment described above, and two fundus image display regions 350, 360 that are smaller in size than the fundus image display region 304. A UWF fundus image is displayed in the fundus image display region 304 in the selected projection, and UWF fundus images are displayed in the fundus image display regions 350, 360 in the projections that have not been selected.

In the first modified example, the coordinate data for the two-dimensional coordinate data of the UWF fundus image obtained by the ophthalmic imaging device 110 is convened into three-dimensional spherical surface coordinate data for the three-dimensional spherical surface coordinates, and the converted three-dimensional spherical surface coordinate data is converted in advance into coordinate data of two-dimensional coordinate data according to the equal-area projection, coordinate data of two-dimensional coordinate data according to the equidistant projection, and coordinate data of two-dimensional coordinate data according to the conformal projection. The UWF fundus images are then displayed in the fundus image display regions 304, 350, 360 employing the image data corresponding to the respective display modes.

Second Modified Example

Explanation follows regarding a second modified example. In the exemplary embodiment described above and the first modified example, in cases in which the fundus image display screen 300 is displayed in the equidistant display mode as illustrated in FIG. 8, the distance between two specified points is calculated based on the image data corresponding to the equidistant display mode. In cases in which the fundus image display screen 300 is displayed in the equal-area display mode as illustrated in FIG. 9, the surface area of a specified region is calculated based on the image data corresponding to the equal-area display mode. However, the technology disclosed herein is not limited thereto, and a distance or surface area of an area may be calculated and displayed on the fundus image display screen 300 when in the conformal display mode, the surface area of an area may be calculated and displayed in addition to a distance on the fundus image display screen 300 when in the equidistant display mode, or a distance may be calculated and displayed in addition to the surface area of an area on the fundus image display screen 300 of the equidistant display mode.

Figure 11:
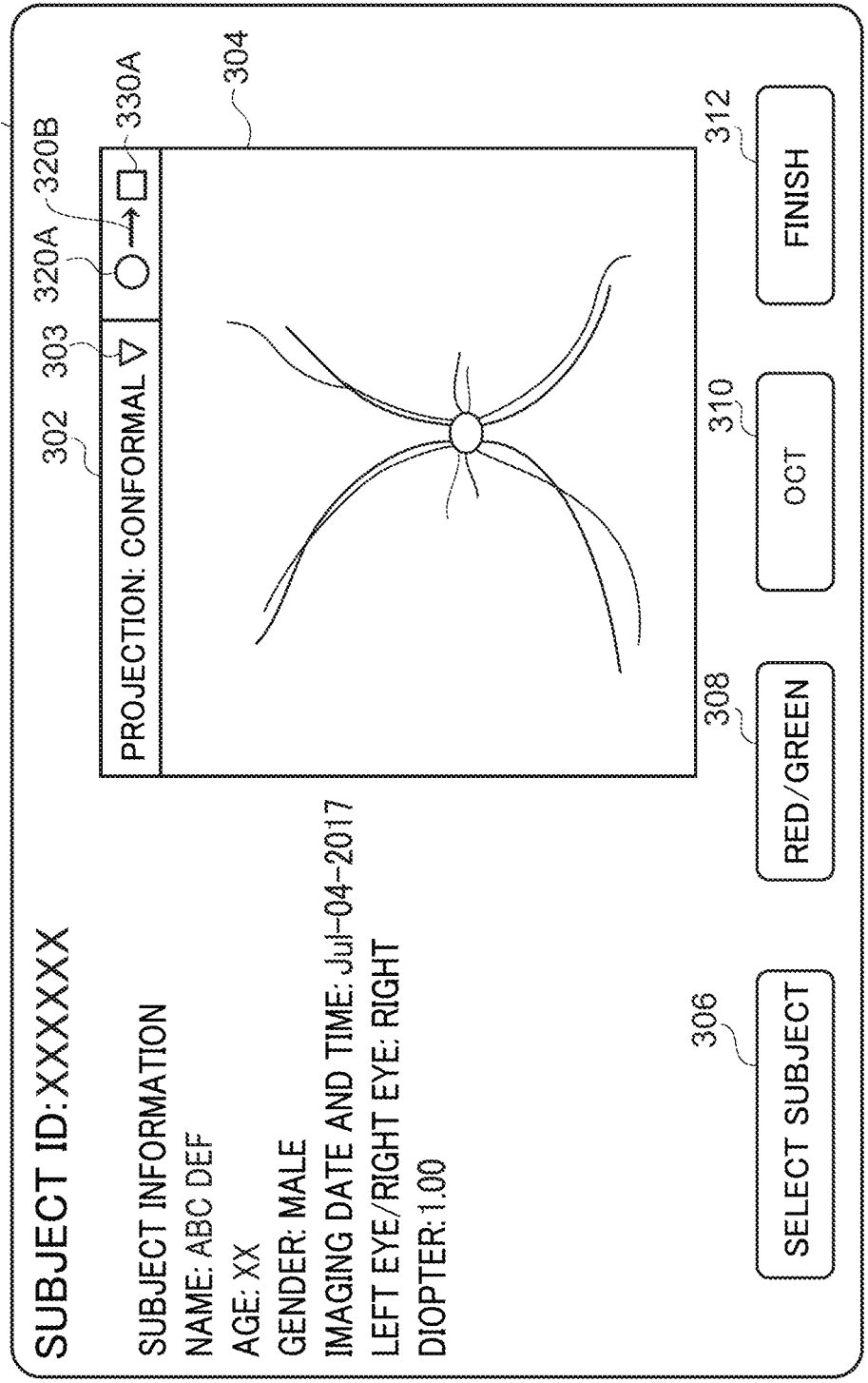
FIG. 11 is a diagram illustrating a fundus image display screen 300 in a conformal display mode in which a UWF fundus image is displayed in a conformal projection in a second modified example.

For example, as illustrated in FIG. 11, when the fundus image display screen 300 is in the conformal display mode in the second modified example, a region displaying the point specify button 320A, the distance calculation button 320B, and the area specify button 330A is provided next to the projection selection region 302. Although not illustrated in the drawings, the fundus image display screen 300 in the equidistant display mode and the fundus image display screen 300 in the equal-area display mode are similarly provided with a region displaying the point specify button 320A, the distance calculation button 320B, and the area specify button 330A next to the projection selection region 302.

In the fundus image display screen 300 in each of the conformal display mode, the equidistant display mode, and the equal-area display mode, when two points are specified as in the exemplary embodiment described above, the distance between the two specified points may be calculated based on the image data corresponding to the equidistant display mode. When an area is specified, the surface area of the specified area may be calculated based on the image data corresponding to the equal-area display mode to display calculated values as desired. Similarly to in the first modified example, in the second modified example two-dimensional coordinate image data of the UWF fundus image obtained by the ophthalmic imaging device 110 in the first modified example is converted into the virtual spherical surface image data with the three-dimensional spherical surface coordinates, and the converted virtual spherical surface image data is converted into image data of the equal-area projection, the equidistant projection, and the conformal projection in advance. The distances and surface areas referred to above are calculated based on this converted image data.

Third Modified Example

In the above exemplary embodiment and the first and second modified examples, the UWF fundus image is displayed as a fundus image. However, the technology disclosed herein is not limited thereto, and a fundus image covering a smaller range than a UWF fundus image may be displayed.

Fourth Modified Example

The above exemplary embodiment and the first to third modified examples are provided with the ophthalmic imaging device 110, the image management server 140, and the image viewer 150. However, the technology disclosed herein is not limited thereto, and may be applied to a first system configuration from which the image management server 140 is omitted, a second system configuration from which the image viewer 150 is omitted, or a third system configuration from which both the image management server 140 and the image viewer 150 are omitted.

In the first system configuration, since the image management server 140 is omitted, fundus images of each of plural subjects obtained by the ophthalmic imaging device 110 are managed by the ophthalmic imaging device 110 or the image viewer 150. In cases in which the fundus images of each of the plural subjects are managed by the ophthalmic imaging device 110, the image viewer 150 acquires the fundus images from the ophthalmic imaging device 110 and executes the fundus image display program.

In the second system configuration, since the image viewer 150 is omitted, fundus images of each of plural subjects obtained by the ophthalmic imaging device 110 are managed by the ophthalmic imaging device 110 or the image management server 140. In cases in which the fundus images of each of the plural subjects are managed by the ophthalmic imaging device 110, the image management server 140 acquires the fundus images from the ophthalmic imaging device 110 and executes the fundus image display program.

In the third system configuration, since both the image management server 140 and the image viewer 150 are omitted, fundus images of each of plural subjects obtained by the ophthalmic imaging device 110 are stored in a storage device by the ophthalmic imaging device 110, and the ophthalmic imaging device 110 acquires the fundus images from the storage device and executes the fundus image display program.

Fifth Modified Example

In the above exemplary embodiment and the first and second modified examples, the UWF fundus image is displayed as the fundus image. However, the technology disclosed herein is not limited thereto, and a montage fundus image may be configured by merging together plural fundus images. Planar images (en-face images) obtained by processing OCT data acquired using the OCT imaging system function or planar images obtained by OCT-angiography may also be employed.

Sixth Modified Example

In a sixth modified example, the acquisition section 172, the selection section 174, the conversion section 176, and the processing section 178 of the CPU 162 execute a fundus image display program illustrated in FIG. 12 instead of the fundus image display program illustrated in FIG. 5.

The fundus image display program illustrated in FIG. 12 is started when the fundus image display screen 300 illustrated in FIG. 6 is displayed on the display section 156.

At step 402, similarly to at step 202, the acquisition section 172 acquires a UWF fundus image corresponding to the subject ID from the image management server 140 via the communication interface (I/F) 158 as a first fundus image.

At step 404, the selection section 174 determines whether or not a display mode has been selected. Specifically, in cases in which the item display instruction button 303 in FIG. 6 has been clicked to display the pulldown menu for the three projections as illustrated in FIG. 7, and the user has clicked the conformal projection instruction button 303A, the equal-area projection instruction button 303B, or the equidistant projection instruction button 303C, the selection section 174 determines that the corresponding mode out of the conformal display mode, the equal-area display mode, or the equidistant display mode has been selected.

At step 406, the conversion section 176 converts the first fundus image into a second fundus image according to the selected display mode. Specifically, similarly to at step 206, the conversion section 176 converts the first fundus image into virtual spherical surface image data based on an eyeball model. In cases in which the equidistant display mode has been selected, the conversion section 176 converts the virtual spherical surface image data into the equidistant image data format according to the equidistant projection similarly to at step 214, to obtain the second fundus image. In cases in which the equal-area display mode has been selected, the conversion section 176 converts the virtual spherical surface image data into the equal-area image data format according to the equal-area projection similarly to at step 226, to obtain the second fundus image. In cases in which the conformal display mode has been selected, the conversion section 176 converts the virtual spherical surface image data into the conformal image data format according to the conformal projection similarly to at step 238, to obtain the second fundus image.

At step 408, the processing section 178 displays the second fundus image obtained by the conversion performed at step 406 in the fundus image display region 304, and also outputs a signal to generate the fundus image display screen 300 in the selected display mode to the display section 156. The display section 156 displays the second fundus image obtained by the conversion performed at step 406 in the fundus image display region 304 and displays the fundus image display screen 300 in the selected display mode. In cases in which the equidistant display mode has been selected, the fundus image display screen 300 is displayed in the equidistant display mode similarly to at step 216. In cases in which the equal-area display mode has been selected, the fundus image display screen 300 is displayed in the equal-area display mode similarly to at step 228. In cases in which the conformal display mode has been selected, the fundus image display screen 300 is displayed in the conformal display mode similarly to at step 242.

In the sixth modified example, an image corresponding to either the equal-area display mode, the equidistant display mode, or the conformal display mode may be acquired as the first fundus image at step 402 (FIG. 12). Specifically, first, the acquisition section 172 acquires the UWF fundus image corresponding to the subject ID from the image management server 140 through the communication interface (I/F) 158, similarly to at step 202. Similarly to at step 206, the conversion section 176 then calculates (converts) the image data of the UWF fundus image acquired at step 202 into virtual spherical surface image data using a three-dimensional spherical surface coordinate format. In cases in which the equidistant display mode has been specified in advance, similarly to at step 214, the conversion section 176 acquires the first fundus image by converting the virtual spherical surface image data into the equidistant image data format according to the equidistant projection. In cases in which the equal-area display mode has been specified in advance, similarly to at step 226, the conversion section 176 acquires the first fundus image by converting the virtual spherical surface image data into the equal-area image data format according to the equal-area projection. In cases in which the conformal display mode has been specified in advance, similarly to at step 238, the conversion section 176 acquires the first fundus image by converting the virtual spherical surface image data into the conformal image data format according to the conformal projection.

Seventh Modified Example

In a seventh modified example, the acquisition section 172, the selection section 174, the conversion section 176, and the processing section 178 of the CPU 162 execute the fundus image display program illustrated in FIG. 13 instead of the fundus image display program illustrated in FIG. 5.

The fundus image display program illustrated in FIG. 13 is started when the fundus image display screen 300 in FIG. 6 has been displayed on the display section 156.

At step 412, similarly to at step 202 (step 402), the acquisition section 172 acquires a UWF fundus image corresponding to the subject ID from the image management server 140 via the communication interface (I/F) 158 as a first fundus image.

At step 414, the selection section 174 determines whether or not an analysis mode has been selected.

An analysis mode is a mode in which image analysis is performed on the fundus image and the results thereof are displayed. For example, analysis modes include an analysis mode for the direction of the optic nerve, an analysis mode to find the size of a lesion (the surface area of a lesion), and an analysis mode to find the distance between structures on the fundus (for example the distance between the macula and the optic nerve head).

In the seventh modified example, an analysis mode instruction button is displayed instead of the item display instruction button 303 in FIG. 6 (the pulldown menu including the conformal projection instruction button 303A, the equal-area projection instruction button 303B, and the equidistant projection instruction button 303C in FIG. 7). When the analysis mode instruction button is clicked, an instruction button for the analysis mode for the direction of the optic nerve, an instruction button for the analysis mode to find the size of a lesion, and an instruction button for the analysis mode to find the distance between structures on the fundus are displayed in a pulldown menu. When the user turns on any of the instruction buttons, the selection section 174 determines that the corresponding analysis mode has been selected.

At step 416, the conversion section 176 converts the first fundus image into a second fundus image according to the selected analysis mode.

Image data in an appropriate display mode for the corresponding analysis mode is specified for each of the analysis modes.

In the analysis mode to find the distance between structures on the fundus, equidistant image data is appropriate since distances are to be calculated. In cases in which the analysis mode to find the distance between structures on the fundus has been selected, the conversion section 176 converts the virtual spherical surface image data into the equidistant image data format according to the equidistant projection similarly to at step 214, to obtain the second fundus image.

In the analysis mode for the size of a lesion, equal-area image data is appropriate since surface area is to be calculated. In cases in which the analysis mode for the size of a lesion has been selected, the conversion section 176 converts the virtual spherical surface image data into the equal-area image data format according to the equal-area projection similarly to at step 226, to obtain the second fundus image.

In the analysis mode for direction, conformal image data is appropriate since direction is to be calculated. In cases in which the analysis mode for direction has been selected, the conversion section 176 converts the virtual spherical surface image data into the conformal image data format according to the conformal projection similarly to at step 238, to obtain the second fundus image.

At step 418, the processing section 178 displays the second fundus image obtained by the conversion performed at step 416 in the fundus image display region 304, and also outputs a signal to generate the fundus image display screen 300 in the selected analysis mode to the display section 156. The display section 156 displays the second fundus image obtained by the conversion performed at step 406 in the fundus image display region 304 and displays the fundus image display screen 300 in the selected analysis mode.

In cases in which the analysis mode to find the distance between structures on the fundus has been selected, the fundus image display screen 300 is displayed in the equidistant display mode similarly to at step 216.

In cases in which the analysis mode for the size of a lesion has been selected, the fundus image display screen 30) is displayed in the equal-area display mode similarly to at step 228.

In cases in which the analysis mode for direction has been selected, the fundus image display screen 300 is displayed in the conformal display mode similarly to at step 242.

Note that in the seventh modified example, at step 412, an image in any mode out of the equal-area display mode, the equidistant display mode, or the conformal display mode may be acquired as the first fundus image. Specifically, first the acquisition section 172 acquires the UWF fundus image corresponding to the subject ID from the image management server 140 through the communication interface (I/F) 158, similarly to at step 202. Similarly to at step 206, the conversion section 176 then calculates (converts) the image data of the UWF fundus image acquired at step 202 into virtual spherical surface image data using a three-dimensional spherical surface coordinate format based on an eyeball model. In cases in which the equidistant display mode has been specified in advance, similarly to at step 214, the conversion section 176 acquires the first fundus image by converting the virtual spherical surface image data into the equidistant image data format according to the equidistant projection. In cases in which the equal-area display mode has been specified in advance, similarly to at step 226, the conversion section 176 acquires the first fundus image by converting the virtual spherical surface image data into the equal-area image data format according to the equal-area projection. In cases in which the conformal display mode has been specified in advance, similarly to at step 238, the conversion section 176 acquires the first fundus image by converting the virtual spherical surface image data into the conformal image data format according to the conformal projection.

The processing section of the CPU 162 of the image viewer 150 calculates the distance between two specified points based on the equidistant image data converted based on equidistant projection when in the equidistant mode.

The processing section of the CPU 162 of the image viewer 150 calculates the surface area of a specified region based on the equal-area image data converted based on equal-area projection when in the equal-area mode.

The processing section of the CPU 162 of the image viewer 150 calculates the direction of a line segment defined by two specified points or an angle defined by three points based on the conformal image data converted based on conformal projection when in the conformal mode.

Eighth Modified Example

In an eighth modified example, the acquisition section 172, the selection section 174, the conversion section 176, and the processing section 178 of the CPU 162 execute the fundus image display program illustrated in FIG. 14 instead of the fundus image display program illustrated in FIG. 5.

At step 422, similarly to at step 202 (step 402, step 412), the acquisition section 172 acquires a UWF fundus image corresponding to the subject ID from the image management server 140 via the communication interface (I/F) 158 as a first fundus image.

At step 424, the conversion section 176 converts the first fundus image into virtual spherical surface image data, and generates respective fundus images for the equal-area display mode, the equidistant display mode, and the conformal display mode from the virtual spherical surface image data.

Specifically, first, similarly to at step 206, the conversion section 176 converts the image data of the UWF fundus image acquired at step 422 into virtual spherical surface image data based on an eyeball model.

Next, similarly to at step 214, the conversion section 176 generates an equidistant image by converting the virtual spherical surface image data into the equidistant image data format according to the equidistant projection.

Similarly to at step 226, the conversion section 176 generates an equal-area image by converting the virtual spherical surface image data into the equal-area image data format according to the equal-area projection.

Similarly to at step 238, the conversion section 176 generates a conformal image by the conversion section 176 converting the virtual spherical surface image data into the conformal image data format according to the conformal projection.

At step 426, the processing section 178 stores the first fundus image, the equidistant image, the equal-area image, and the conformal image associated with each other in the memory (the RAM 166).

At step 428, the selection section 174 determines whether or not the user has selected a display mode or an analysis mode. In the eighth modified example, in cases in which a display mode has been selected at step 428, determination is similar to that at step 404 (see FIG. 12). Moreover, in the eighth modified example, in cases in which an analysis mode has been selected at step 428, determination is similar to that at step 414 (see FIG. 13).

At step 430, the processing section 178 outputs a signal to generate the fundus image display screen 300 in the display mode or analysis mode selected at step 428 to the display section 156. The display section 156 displays the fundus image display screen 300) in the selected display mode or analysis mode.

Ninth Modified Example

In a ninth modified example, the acquisition section 172, the conversion section 176, and the processing section 178 of the CPU 162 may be configured so as to execute the following processing instead of the fundus image display program illustrated in FIG. 5.

Similarly to at step 202, the acquisition section 172 acquires a UWF fundus image corresponding to the subject ID from the image management server 140 via the communication interface (I/F) 158 as a first fundus image.

Similarly to at step 204, the processing section 178 outputs an image signal of the UWF fundus image to the display section 156. The display section 156 displays the UWF fundus image as-is on the fundus image display region 304 based on the output image signal.

When the user has specified two points and input an instruction to calculate the distance between the two specified points on the displayed UWF fundus image, the conversion section 176 converts the image data of the UWF fundus image into virtual spherical surface image data, and converts the virtual spherical surface image data into the equidistant image data format according to the equidistant projection. The processing section calculates the distance between the two specified points based on the equidistant image data converted based on equidistant projection in the equidistant mode, and outputs a value for the distance between the two points to the display section 156. The display section 156 displays the two points along with the distance between the two points.

When the user has specified a region and input an instruction to calculate the surface area of the specified region on the displayed UWF fundus image, the conversion section 176 converts the image data of the UWF fundus image into virtual spherical surface image data based on an eyeball model, and converts the virtual spherical surface image data into the equal-area image data format according to the equal-area projection. The processing section calculates the surface area of the specified region based on the equal-area image data converted based on equal-area projection in the equal-area mode, and outputs a value for the surface area of the specified region to the display section 156. The display section 156 displays the specified region along with the value for the surface area of the specified region.

When the user has specified two points or three points and input an instruction regarding the direction of a line segment defined by the two specified points or an angle defined by the specified three points in the displayed UWF fundus image, the conversion section 176 converts the image data of the UWF fundus image into virtual spherical surface image data, and converts the virtual spherical surface image data into the conformal image data format according to the conformal projection. The processing section calculates the direction of the line segment defined by the two specified points or the angle defined by the specified three points based on the converted conformal image data based on the conformal projection, and outputs a value expressing the direction of the line segment defined by the two points or the angle defined by the three points to the display section 156. The display section 156 displays the two or three specified points along with the value expressing the direction of the line segment defined by the two points or the angle defined by the three points.

Other Modified Examples

In the above exemplary embodiment and the first to ninth modified examples, the equal-area display mode, the equidistant display mode, and the conformal display mode are employed as the three display modes. However, the technology disclosed herein is not limited thereto, and other display modes such as the following may be employed. Examples include display modes according to Mollweide projection, Mercator projection, Sanson projection, and the like. Moreover, the number of the plural display modes that can be selected may be a plural number of display modes other than three display modes.

In the examples of the first exemplary embodiment and the respective modified examples, control processing is implemented using a computer by software configurations. However, the technology disclosed herein is not limited thereto. For example, instead of software configurations using a computer, the control processing may be executed solely by hardware configurations such as field programmable gate arrays (FPGAs) or application specific integrated circuits (ASICs). The control processing may also be executed by a configuration combining hardware configurations and software configurations.

All cited documents, patent applications, and technical standards mentioned in the present specification are incorporated by reference in the present specification to the same extent as if each individual cited document, patent application, or technical standard was specifically and individually indicated to be incorporated by reference.

Explanation of the Reference Numerals 100 fundus image display system
110 ophthalmic imaging device
130 network
140 image management server
150 image viewer
152 computer body
156 display section
172 acquisition section
174 selection section
176 conversion section
178 processing section
300 fundus image display screen
302 projection selection region
303 item display instruction button 303A conformal projection instruction button
303B equal-area projection instruction button
303C equidistant projection instruction button
304 fundus image display region
320 distance calculation icon region
320A point specify button
320B distance calculation button
330 surface area calculation icon region
330A area specify button
350, 360 fundus image display region

The invention claimed is:

1. An image signal output device, comprising:
   an acquisition section configured to acquire a fundus image;
   a selection section configured to select an analysis mode for analyzing the acquired fundus image from a plurality of analysis modes;
   a conversion section configured to convert the fundus image based on the selected analysis mode from a plurality of projections; and
   a processing section configured to output an image signal of the converted fundus image.

2. The image signal output device of claim 1, wherein the plurality of projections include at least a conformal projection, an equidistant projection, and an equal-area projection.

3. The image signal output device of claim 2, wherein when none of the analysis modes have been selected by the selection section, the processing section outputs an image signal to display the fundus image according to the conformal projection.

4. The image signal output device of claim 2, wherein when the converted fundus image is being displayed in the equidistant projection, the processing section calculates a distance between two specific points and outputs data relating to the calculated distance.

5. The image signal output device of claim 2, wherein when the converted fundus image is being displayed in the equal-area projection, the processing section calculates a surface area of a specific region and outputs data relating to the calculated surface area.

6. The image signal output device of claim 1, wherein when the projection into which the fundus image that has already been converted by the conversion section is selected by the selection section again, the processing section outputs an image signal of the fundus image corresponding to another selected projection and already converted by the conversion section.

* * * * *